US012793815B2

(12) United States Patent
Jeong et al.

(10) Patent No.: US 12,793,815 B2
(45) Date of Patent: Nov. 10, 2026

(54) METHOD AND SYSTEM FOR PREDICTING PLURALITY OF MATERIAL PROPERTIES

(71) Applicant: LG MANAGEMENT DEVELOPMENT INSTITUTE CO., LTD., Seoul (KR)

(72) Inventors: Dae Woong Jeong, Seoul (KR); Sung Moon Ko, Seoul (KR); Su Min Lee, Seoul (KR); Se Hui Han, Seoul (KR)

(73) Assignee: LG MANAGEMENT DEVELOPMENT INSTITUTE CO., LTD., Seoul (KR)

( * ) Notice: Subject to any disclaimer, the term of this patent is extended or adjusted under 35 U.S.C. 154(b) by 0 days.

(21) Appl. No.: 19/429,503

(22) Filed: Dec. 22, 2025

(65) Prior Publication Data

US 2026/0120815 A1 Apr. 30, 2026

Related U.S. Application Data

(63) Continuation of application No. PCT/KR2024/095889, filed on Jun. 24, 2024.

(30) Foreign Application Priority Data

Jun. 23, 2023 (KR) ........................ 10-2023-0080780
Jun. 24, 2024 (KR) ........................ 10-2024-0082143

(51) Int. Cl.
*G16C 20/30* (2019.01)
*G16C 20/70* (2019.01)
(Continued)

(52) U.S. Cl.
CPC ............. *G16C 20/30* (2019.02); *G16C 20/70* (2019.02); *G06N 20/00* (2019.01); *G16C 20/90* (2019.02); *G16C 60/00* (2019.02)

(58) Field of Classification Search
USPC ............................................................ 702/22
See application file for complete search history.

(56) References Cited

U.S. PATENT DOCUMENTS

2019/0279037 A1* 9/2019 Tanimoto .............. G06F 18/232
2022/0358438 A1* 11/2022 Asahara .................. G06F 30/27
(Continued)

FOREIGN PATENT DOCUMENTS

KR 10-2020-0052450 A 5/2020
KR 10-2021-0081518 A 7/2021
(Continued)

OTHER PUBLICATIONS

Kojima et al., "kGCN: a graph-based deep learning framework for chemical structures", Journal of Cheminformatics, pp. 1-10, 2020.
(Continued)

*Primary Examiner* — Paul D Lee
(74) *Attorney, Agent, or Firm* — PnK IP LLC

(57) ABSTRACT

A method for a computing system including at least one memory and at least one processor configured to predict characteristics regarding a plurality of material properties includes: obtaining experimental data including characteristics data on the plurality of material properties regarding materials; pre-training an integrated prediction model for a plurality of tasks of predicting characteristics regarding the plurality of material properties from the obtained experimental data; inputting, to the pre-trained integrated prediction model, material information to be predicted; outputting, by the integrated prediction model, a characteristic value for each of the plurality of material properties in regard to the material information; and providing the output characteristic value for each of the plurality of material properties.

20 Claims, 23 Drawing Sheets

(51) Int. Cl.

| | |
|---|---|
| *G06N 20/00* | (2019.01) |
| *G16C 20/90* | (2019.01) |
| *G16C 60/00* | (2019.01) |

(56) References Cited

U.S. PATENT DOCUMENTS

2022/0359047 A1* 11/2022 Kanazawa ............. G16C 20/30
2023/0081583 A1* 3/2023 Kanazawa ............. G06N 20/00
2023/0419086 A1* 12/2023 Pocajt .................... G06N 3/047
2024/0394258 A1* 11/2024 Chen ................... G06F 16/2455

FOREIGN PATENT DOCUMENTS

KR 10-2023-0040120 A 3/2023
KR 10-2023-0068506 A 5/2023
KR 10-2023-0075601 A 5/2023

OTHER PUBLICATIONS

International Search Report dated Oct. 7, 2024, issued in PCT International Patent Application No. PCT/KR2024/095889.
Written Opinion dated Oct. 7, 2024, issued in International Patent Application No. PCT/KR2024/095889.

* cited by examiner

METHOD AND SYSTEM FOR PREDICTING PLURALITY OF MATERIAL PROPERTIES

CROSS REFERENCE TO RELATED APPLICATIONS

This application is a Bypass Continuation of International Patent Application No. PCT/KR2024/095889, filed on Jun. 24, 2024, which claims priority from and the benefit of Korean Patent Application Nos. 10-2023-0080780, filed on Jun. 23, 2023 and 10-2024-0082143, filed on Jun. 24, 2024, which is hereby incorporated by reference for all purposes as if fully set forth herein.

BACKGROUND

Field

Embodiments of the invention relate generally to a method and system for predicting a plurality of material properties, and more particularly, the present disclosure relates to a method and system for predicting a plurality of material properties of a specific material using a pre-trained integrated prediction model.

Discussion of the Background

Machine learning and artificial intelligence models require large amounts of data. However, realistically, there are limits to always containing sufficient data. This is especially worse when trying to apply the model to new domains or tasks. A representative example of this situation is the molecular structure data set. In the fields of chemistry and pharmacology, data is needed to predict the characteristics of new molecules, but experimental data for each molecule is difficult to obtain and is costly. Accordingly, the need for transfer learning techniques that apply the knowledge of presently trained models to new tasks has increased.

However, existing transfer learning has been developed mainly focusing on classification issues of large-scale data sets such as image or text data. Accordingly, existing transfer learning techniques show limitations when applied to small, complex data sets such as regression problems or molecular data sets. In particular, since molecular structure data is high-dimensional and a relationship of couplings to each composition greatly affects each material property, when transfer learning techniques are applied to the relationship between one material property and molecular structure data and then to the relationship between another material property and molecular structure data, existing Euclidean space-based transfer learning techniques may not effectively handle complex structures in such non-Euclidean spaces.

Riemannian geometry enables calculus in curved spaces, allowing for better representation and analysis of complex structures in data. This Riemannian geometric approach assumes that latent vectors exist on a curved manifold, which is advantageous for aligning the geometry between complex source and target tasks.

Accordingly, based on the above background, it is necessary to introduce a new technology that may demonstrate high prediction performance and stability even on small data sets, implement more effective transfer learning, and improve model normalization performance to enhance regularization performance.

The above information disclosed in this Background section is only for understanding of the background of the inventive concepts, and, therefore, it may contain information that does not constitute prior art.

SUMMARY

An aspect of an embodiment of the present disclosure is directed to providing a method and system for predicting a plurality of material properties that mutually transfers and learns knowledge data of a latent space for each task through geometric alignment in one integrated latent space in order to process a multi-task that predicts an output satisfying a plurality of domains.

Additional features of the inventive concepts will be set forth in the description which follows, and in part will be apparent from the description, or may be learned by practice of the inventive concepts.

According to an embodiment of the present disclosure, a method for a computing system including at least one memory and at least one processor configured to predict characteristics regarding a plurality of material properties includes: obtaining experimental data including characteristics data on the plurality of material properties regarding materials; pre-training an integrated prediction model for a plurality of tasks of predicting characteristics regarding the plurality of material properties from the obtained experimental data; inputting, to the pre-trained integrated prediction model, material information to be predicted; outputting, by the integrated prediction model, a characteristic value for each of the plurality of material properties in regard to the material information; and providing the output characteristic value for each of the plurality of material properties.

The material information may include at least one piece of information of a molecular structural formula, a material name, or a chemical formula. Each of the plurality of material property may include at least one of a boiling point, a melting point, a refractive index, solubility, viscosity, surface tension, density, strength, or thermal conductivity, and the characteristic value for each material property may include a characteristic value or range predicted for the material property.

The pre-training of the integrated prediction model for the plurality of tasks may include training a source task module configured to perform a prediction on a first material property as a source task, training a target task module configured to perform a prediction on a second material property as a target task; mapping a first feature vector to perform the prediction on the first material property to an integrated latent space, and mapping a second feature vector to perform the prediction on the second material property to the integrated latent space.

The method for predicting the plurality of material properties according to an embodiment of the present disclosure further may include computing an integrated loss including a regression loss for training the source task module, an autoencoder loss for training the target task module, and a consistency loss and a mapping loss in a process of mapping the first feature vector to the integrated latent space, and training the integrated prediction model through the integrated loss.

The method for a computing system including at least one memory and at least one processor configured to predict characteristics regarding a plurality of material properties may further include generating a perturbation vector for an embedding vector for the material information; computing a distance loss according to the perturbation vector; and adding the computed distance loss to the integrated loss.

The method for a computing system including at least one memory and at least one processor configured to predict characteristics regarding a plurality of material properties may further include generating a perturbation vector for an embedding vector for the material information, computing a distance loss based on the perturbation vector, and adding the computed distance loss to the integrated loss.

The pre-training of the integrated prediction model for the plurality of tasks may include obtaining a geometric alignment vector, which is a vector that supports geometric alignment between data in one integrated latent space, based on the experimental data, computing a geometric alignment loss based on the obtained geometric alignment vector, and updating parameters of the integrated prediction model based on the computed geometric alignment loss.

The pre-training of the integrated prediction model for the plurality of tasks may include pre-training the integrated prediction model based on material property relationship information between the material properties of the plurality of tasks.

The pre-training of the integrated prediction model based on the material property relationship information may include: obtaining material property relationship data indicating a relationship between the material properties; and storing the obtained material property relationship data in a material property relationship database.

The obtaining of the material property relationship data indicating the relationship between the material properties may include collecting the material property relationship data including the material property relationship information by commanding a pre-trained language model configured to perform a keyword search for the material properties.

The storage of the obtained material property relationship data in the material property relationship database may include extracting the material property relationship information from the material property relationship data through the language model, and classifying, characterizing and storing information on the extracted material property relationship information.

The material property relationship information may include information on the material properties associated with a specific material property, information that determines relationship characteristics such as trade-off, similarity, or correlation when associated, and information indicating the degree of association in the determined relationship characteristics.

The method for predicting the plurality of material properties according to an embodiment of the present disclosure further may include providing a knowledge graph representing the material property relationship information.

The pre-training of the integrated prediction model for the plurality of tasks may include performing pre-training on the integrated prediction model by reflecting the material property relationship information between the material properties of the plurality of tasks.

The method for a computing system including at least one memory and at least one processor configured to predict characteristics regarding a plurality of material properties may further include performing an update on the integrated prediction model for a new task other than the plurality of tasks.

The performance of the update for the new task may include obtaining the experimental data of a predicted target material property of the new task, and training an n-th prediction model added to the pre-trained integrated prediction model through the experimental data of the predicted target material property.

The training of the n-th prediction model through the experimental data of the predicted target material property may include updating the integrated prediction model by training a module included in the n-th prediction model through the experimental data while freezing the module related to a pre-trained task in the integrated prediction model.

The provision of the output characteristic value for each of the plurality of material properties may include inputting the material information into the n-th prediction model to provide the characteristic value for each material property including the characteristic value predicted for a new material property.

According to another embodiment of the present disclosure, a system for predicting a plurality of material properties may include at least one memory; and at least one processor including at least one instruction and configured to train an integrated prediction model by reading out at least one application stored in the memory, in which the at least one processor is configured to obtain experimental data including characteristics data on the plurality of material properties regarding materials, pre-train an integrated prediction model for a plurality of tasks of predicting characteristics regarding the plurality of material properties from the obtained experimental data, input, to the pre-trained integrated prediction model, material information to be predicted, output, by the integrated prediction model, a characteristic value for each of the plurality of material properties in regard to the material information, and provide the output characteristic value for each of the plurality of material properties.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the inventive concepts.

DETAILED DESCRIPTION

Figure 1:
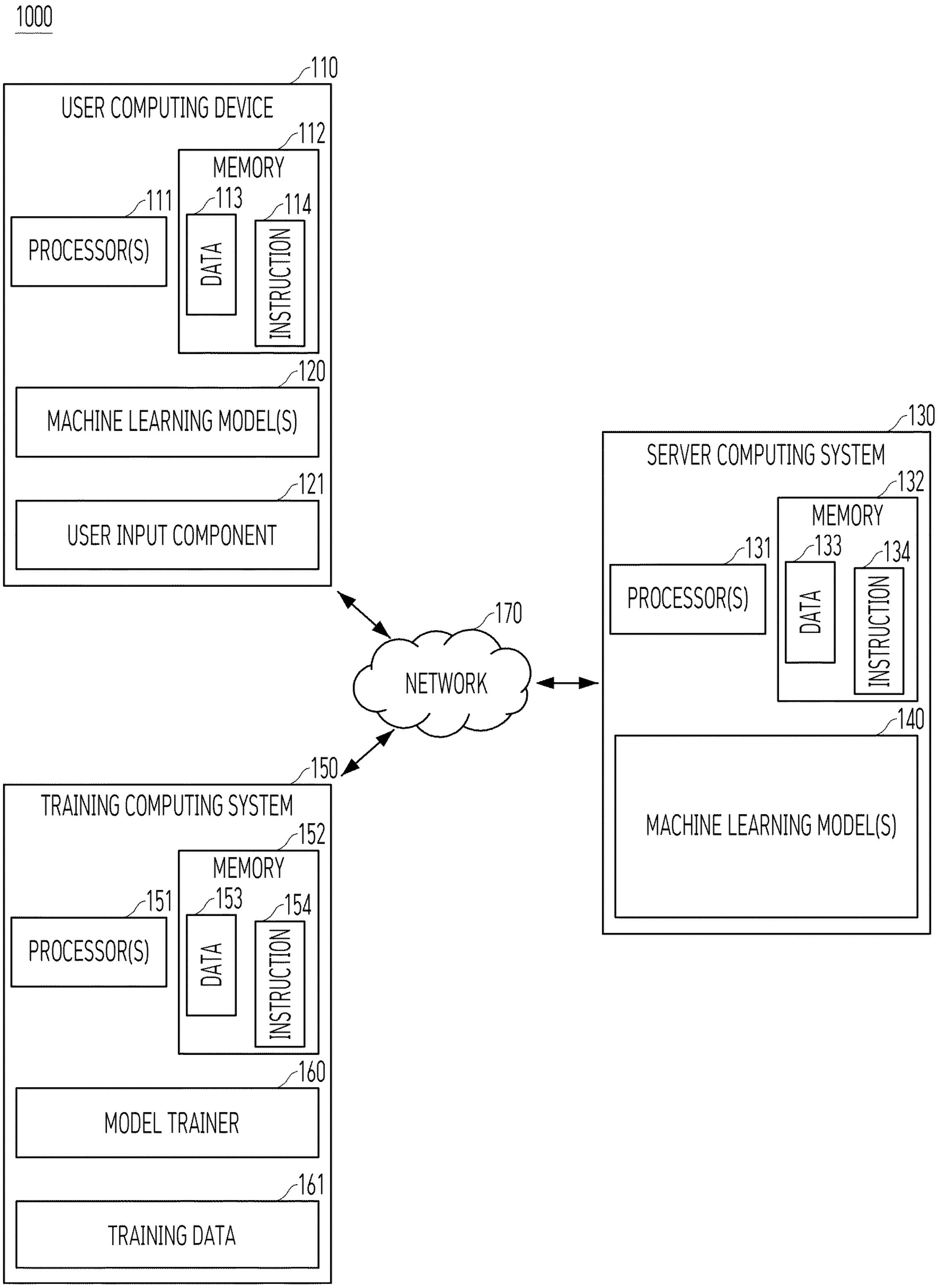
FIG. 1 is a schematic example block diagram illustrating a computing system implementing a multi-tasking learning model provision service according to an embodiment of the present disclosure.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z—axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the scope of the inventive concepts. Further, the blocks, units, and/or modules of some embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Example, System Implementing Multi-Tasking Learning Model Provision Service

Hereinafter, an example, system for implementing a multi-tasking learning model provision service that mutually transfers and learns knowledge data of a latent space for each task through geometric alignment in one integrated latent space in order to process a multi-task for output according to a plurality of domains and performs multi-tasking based thereon is described in detail with reference to the attached drawings.

FIG. 1 is a schematic example block illustrating a computing system implementing a multi-tasking learning model provision service according to an embodiment of the present disclosure.

Referring to FIG. 1, a computing system 1000 which implements the multi-tasking learning model provision service according to an embodiment of the present disclosure may include a user computing device 110, a server computing system 130, and a training computing system 150, and any other devices which are configured to communicate through a network 170.

A multi-tasking model training method and a multi-tasking performing method using a machine learning model trained based thereon according to an embodiment of the present disclosure may be implemented and provided locally by the user computing device 110, implemented and provided in the form of a web service by the server computing system 130 which communicates with the user computing device 110, and implemented and provided by mutual association of the user computing device 110 and the server computing system 130.

The user computing device 110 and/or the server computing system 130 may train a machine learning model 120 and/or 140 through interaction with the training computing system 150 communicationally connected through the network 170. The training computing system 150 may be a system separated from the server computing system 130 or may be a portion of the server computing system 130.

In addition, the artificial intelligence model may be trained (or directly trained) locally by the user computing device 110, trained while the server computing system 130 and the user computing device 110 interact with each other through the network 170, and trained using various training techniques and learning techniques by the separate training computing system 150. In addition, the method may also be implemented by a method in which the artificial intelligence model trained by the training computing system 150 is transmitted to the user computing device 110 and/or the server computing system 130 through the network 170, and is provided and updated.

In some embodiments, the training computing system 150 may be a portion of the server computing system 130 or a portion of the user computing device 110.

The user computing device 110 may include various types of computing devices such as a smart phone, a cellular phone, a digital broadcasting device, personal digital assistants (PDA), a portable multimedia player (PMP), a desktop, a wearable device, an embedded computing device, and/or a tablet PC.

The user computing device 110 may include at least one processor 111 and at least one memory 112. Herein, the processor 110 may include at least one at least one processor electrically connected among a central processing unit (CPU), a graphics processing unit (GPU), application specific integrated circuits (ASICs), digital signal processors (DSPs), digital signal processing devices (DSPDs), programmable logic devices (PLDs), field programmable gate arrays (FPGAs), controllers, micro-controllers, microprocessors, and/or other electrical units to perform functions.

The memory 112 may include at least one non-transitory/transitory computer-readable storage media, such as RAM, ROM, EEPROM, EPROM, flash memory devices, or magnetic disks, and combinations thereof, and may include web storage of servers performing storage functions of the memory on the Internet. The memory 112 may store data 113 and instruction (or instructions) 114 necessary for the at least one processor 111 configured to perform a functional operation, such as training the artificial intelligence model or executing multi-tasking learning through the artificial intelligence model.

The user computing device 110 may store at least one machine learning model 120.

Particularly, the user computing device 110 may be various machine learning models such as a plurality of neural networks (for example, deep neural networks) or other types of machine learning models, including non-linear models and/or linear models, and may be configured of a combination thereof.

In this case, the neural network may include at least one of feed-forward neural networks, recurrent neural networks (for example, long short-term memory recurrent neural networks), convolutional neural networks and/or other forms of neural networks.

The user computing device 110 may receive at least one machine learning model 120 from the server computing system 130 via the network 170, store the same in the memory 112, and then execute the stored machine learning model 120 by the processor 111 configured to perform the multi-tasking learning.

In another embodiment, the server computing system 130 may include at least one machine learning model 140 and perform operations through the machine learning model 140, and may provide the multi-tasking learning model provision service to a user by linking with the user computing device 110 in a manner of communicating data related thereto with the user computing device 110.

For example, the user computing device 110 may perform the multi-tasking learning model provision service by providing an output for the input of a user using the machine learning model 140 through the server computing system 130 via the web.

In addition, the artificial intelligence model may also be implemented in such a way that at least some of the machine learning models 120 and/or 140 are executed on the user computing device 110 and the rest are executed on the server computing system 130.

In addition, the user computing device 110 may include at least one input component 121 that detects user input. For example, the user input component 121 may include a touch sensor (for example, a touch screen and/or a touch pad) that detects touch of an input medium of a user (for example, a finger or a stylus), an image sensor that detects a motion input of a user, a microphone, a button, a mouse and/or a keyboard that detects user voice input. In addition, the user input component 121 may include an interface and an external controller when receiving input from an external controller (for example, a mouse or a keyboard) through the interface.

The server computing system 130 may include at least one processor 131 and at least one memory 132. Herein, the at least one processor 131 may include at least one processor electrically connected among a central processing unit (CPU), a graphics processing unit (GPU), application specific integrated circuits (ASICs), digital signal processors (DSPs), digital signal processing devices (DSPDs), programmable logic devices (PLDs), field programmable gate arrays (FPGAs), controllers, micro-controllers, microprocessors, and/or other electrical units to perform functions.

In addition, the memory 132 may include at least one non-transitory/transitory computer-readable storage media, such as RAM, ROM, EEPROM, EPROM, flash memory devices, or magnetic disks, and combinations thereof. The memory 132 may store data 133 and instruction (or instructions) 134 required for the processors 131 configured to perform a functional operation such as the train of the artificial intelligence model or the execution of the multi-tasking learning through the artificial intelligence model.

The server computing system 130 may be implemented to include at least one computing device or computer. For example, the server computing system 130 may be implemented so that a plurality of computing devices operates according to sequential computing architecture, parallel computing architecture, or a combination thereof. Further, the server computing system 130 may include a plurality of computing devices connected through the network 170.

Further, the server computing device 130 may store at least one machine learning model 140. For example, the server computing system 130 may include a neural network and/or multilayer non-linear model as the machine learning model 140. An example, neural network may include a feed-forward neural network, a deep neural network, a recurrent neural network, and a convolution neural network.

The training computing system 150 may include at least one processor 151 and at least one memory 152. Herein, the processor 151 may include at least one processor electrically connected among the CPU, the GPU, the ASICs, the DSPs, the DSPDs, the PLDs, the FPGAs, controllers, micro-controllers, microprocessors, and/or other electrical units to perform functions.

In addition, the memory 152 may include at least one non-transitory/transitory computer-readable storage media, such as RAM, ROM, EEPROM, EPROM, flash memory devices, or magnetic disks, and combinations thereof, and may include web storage of servers performing storage functions of the memory on the Internet. The memory 152 may store data 153 and instruction (or instructions) 154 necessary for the processor 151 configured to perform training of the artificial intelligence model.

Figure 3:
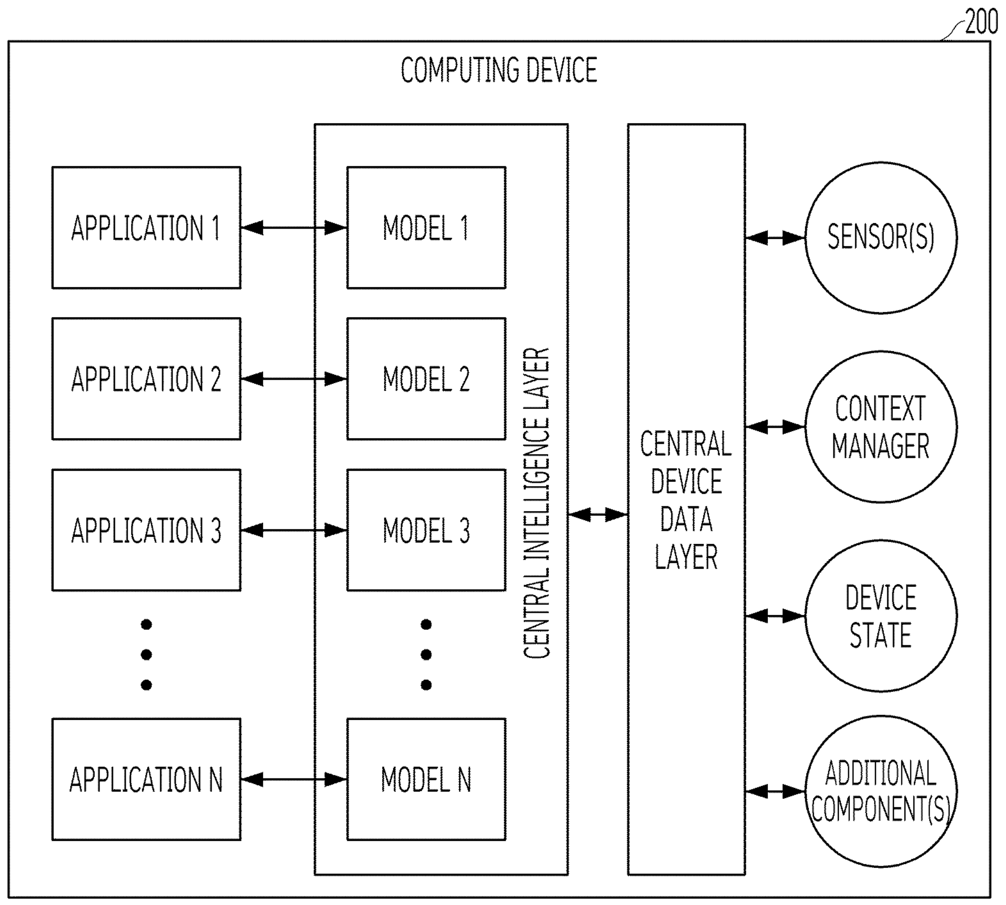
FIG. 3 is a schematic example block illustrating another aspect illustrating a computing device implementing a multi-tasking learning model provision service according to an embodiment of the present disclosure.

For example, the training computing system 150 may include a model trainer 160 configured to train the machine learning models 120 and/or 140 stored in the user computing device 110 and/or the server computing system 130 using various training or learning techniques such as backpropagation of an error according to the framework illustrated in FIG. 3.

For example, the model trainer 160 may perform updating at least one parameter of the machine learning model 120 and/or 140 based on a defined loss function by a backpropagation scheme.

In some implementation examples, the performance of the backpropagation of the error may include performing truncated backpropagation through time. The model trainer 160 may perform multiple generalization techniques (for example, weight reduction, drop-out, and/or knowledge distillation) in order to enhance a generalization capability of the trained machine learning models 120 and/or 140.

In particular, the model trainer 160 may train the machine learning models 120 and/or 140 based on a series of training data 161. Herein, the training data 161 may include, for example, different formats of data such as an image, an audio, and/or text. Examples of image type data which may be used may include a video frame, LiDAR point cloud, an X-ray image, a computer tomography scan, a hyperspectral image, and/or various other types of images.

The training data 161 may be provided by the user computing device 110 and/or the server computing system 130. When the training computing device 150 trains the machine learning models 120 and/or 140 with respect to specific data of the user computing device 110, the machine learning models 120 and/or 140 may be characterized as a personalized model.

In addition, the model trainer 160 may include a computer logic utilized to provide a desired function.

Further, the model trainer 160 may be implemented as hardware, firmware, and/or software controlling a universal processor. In one implementation example, the model trainer 160 may include a program file stored in a storage device, and may be loaded to the memory 152 and executed by at least one processor 151. In another implementation example, the model trainer 160 may include at least one set of computer-executable data 153 and instruction 154 stored in executable by a tangible computer-readable storage medium such as a RAM hard disk or an optical or magnetic medium.

The network 170 may include a 3rd Generation Partnership Project (3GPP) network, a Long Term Evolution (LTE) network, a World Interoperability for Microwave Access (WIMAX) network, Internet, a Local Area Network (LAN), Wireless Local Area Network (LAN), a Wide Area Network (WAN), a Personal Area Network (PAN), a Bluetooth network, a satellite broadcasting network, an analog broadcasting network, and/or a Digital Multimedia Broadcasting (DMB) network, but is not limited thereto.

In general, communication through the network 170 may be performed through various communication protocols (for example, TCP/IP, HTTP, SMTP, and/or FTP), encoding or formats (for example, HTML and/or XML), and/or protective schemas (for example, VPN, secure HTTP, and/or SSL) using any type of wired and/or wireless communication.

Figure 2:
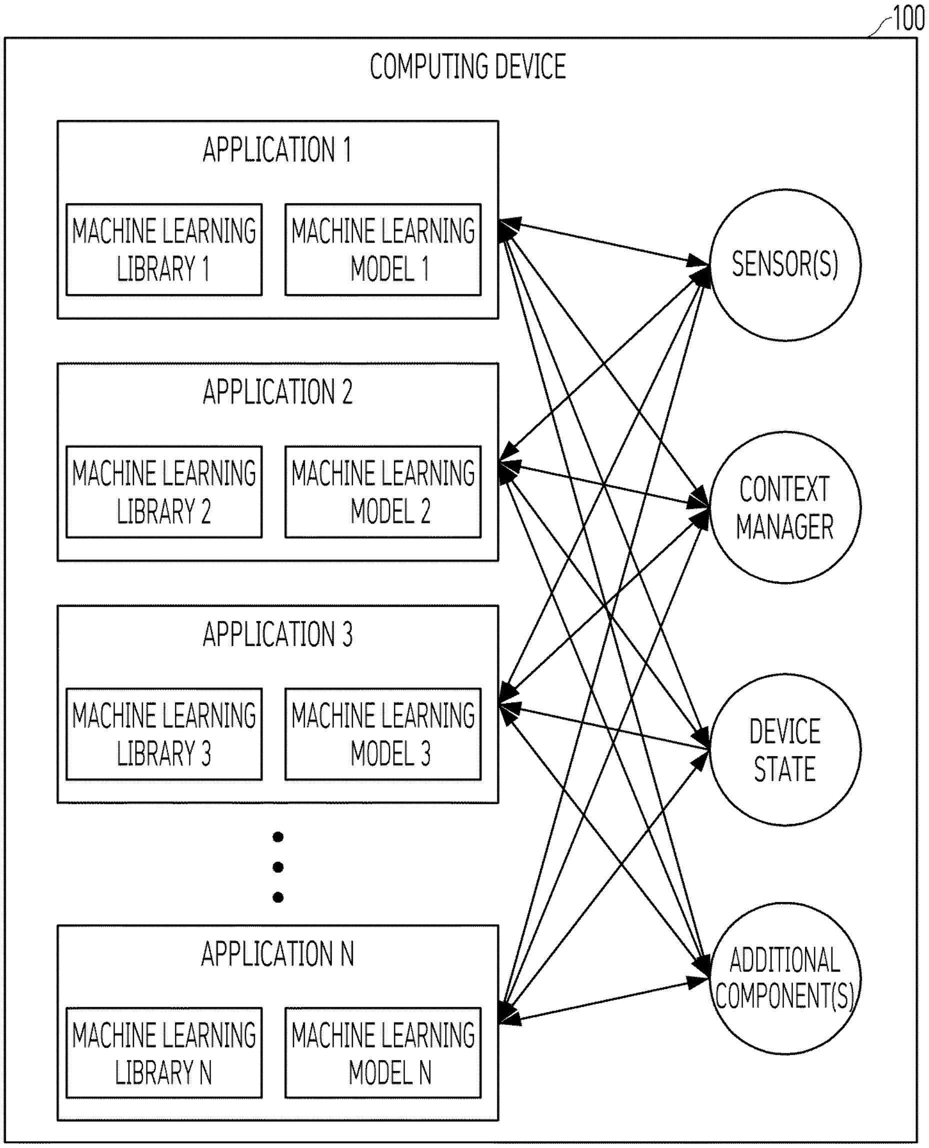
FIG. 2 is a schematic example block diagram illustrating a computing device implementing a multi-tasking learning model provision service according to an embodiment of the present disclosure.

FIG. 2 is a schematic example block illustrating a computing device implementing a multi-tasking learning model provision service according to an embodiment of the present disclosure.

Referring to FIG. 2, the computing device 100 included in the user computing device 110, the server computing system 130, and the training computing system 150 may include a plurality of applications (for example, application 1 to application N). Each application may include a machine learning library and at least one machine learning model. For example, the applications may include an image processing (for example, detection, classification and/or segmentation) application, a text messaging application, an e-mail application, a dictation application, a virtual keyboard application, a browser application, and a chat-bot application.

The computing device 100 may include the model trainer 160 for training the artificial intelligence model, and may store and operate the trained artificial intelligence model to provide output data according to predetermined input data (in an embodiment, material unique characteristic information and/or material physical property specific information).

Each application of the computing device 100 may communicate with a number of other components of the computing device, such as, for example, at least one sensor, a context manager, a device state component, and/or additional components. In an embodiment, each application may communicate with each device component using an API (for example, a public API). The API used by each application may be specific to the relevant application.

FIG. 3 is a schematic example block illustrating another aspect of a computing device implementing a multi-tasking learning model provision service according to an embodiment of the present disclosure.

Referring to FIG. 3, a computing device 200 may include a plurality of applications (for example, application 1 to application N). Each application may be in communication with a central intelligence layer. For example, the applications may include an image processing application, a text messaging application, an e-mail application, a dictation application, a virtual keyboard application, and a browser application. In an embodiment, each application may communicate with the central intelligence layer (and model(s) stored therein) using an API (for example, a common API across all applications).

In addition, the central intelligence layer may include a plurality of machine learning models. For example, as illustrated in FIG. 3, a respective machine learning model and at least some thereof may be provided for each application and managed by the central intelligence layer. In other embodiments, two or more applications may share a single machine leaning model. For example, the central intelligence layer may provide a single model for all of the applications. In some embodiments, the central intelligence layer may be included within an operating system of the computing device 200 or implemented differently.

The central intelligence layer may communicate with a central device data layer. The central device data layer may be a centralized data storage for the computing device 200. As illustrated in FIG. 3, the central device data layer may communicate with a number of other components of the computing device 200, such as, for example, at least one sensor, a context manager, a device state component, and/or additional components. In other embodiments, the central device data layer may communicate with each device component using an API (for example, a private API).

The technology discussed herein may refer to servers, databases, software applications, and other computer-based systems, as well as actions taken and information sent to and from such systems. The inherent flexibility of computer-based systems may allow for a great variety of possible configurations, combinations, and divisions of tasks and functionality between and among components. For instance, processes discussed herein may be implemented using a single device or component or a plurality of devices or components working in combination. Databases and applications may be implemented on a single system or distributed across a plurality of systems. Distributed components may operate sequentially or in parallel.

[Multi-Tasking Learning Model (MtLM)]

Figure 4:
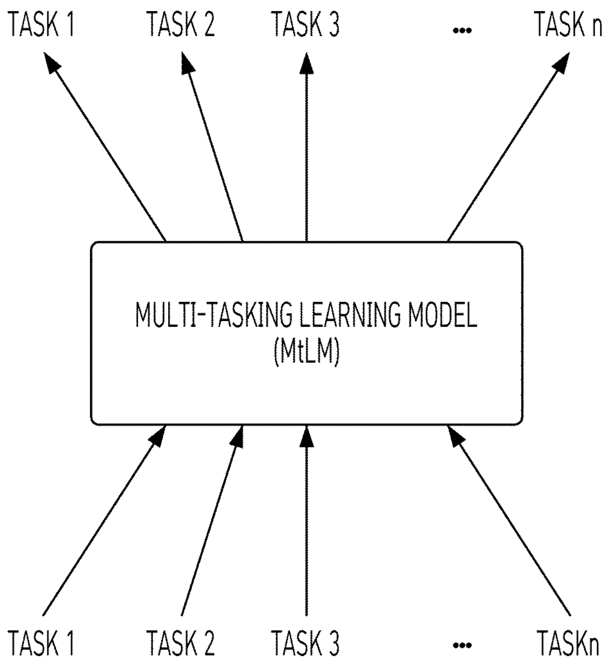
FIGS. 4 and 5 are schematic example conceptual diagrams illustrating a multi-tasking learning model according to an embodiment of the present disclosure.
Figure 5:
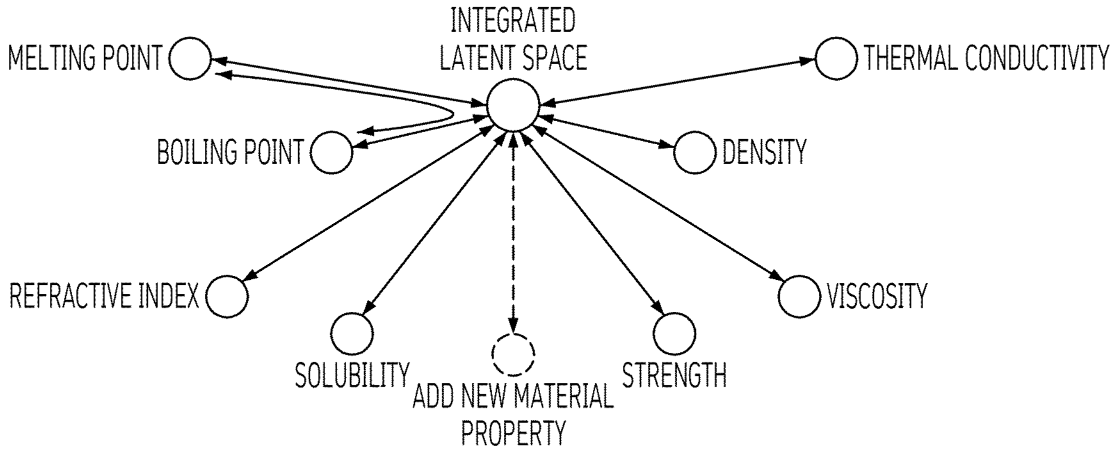

FIGS. 4 and 5 are schematic example conceptual illustrating the MtLM according to an embodiment of the present disclosure.

Referring to FIGS. 4 and 5, the MtLM (geometrically aligned transfer encoder model) according to an embodiment of the present disclosure may be a machine learning model that mutually aligns fragmented knowledge data (a latent vector) in a latent space for each task through geometric transfer in one integrated latent space (M: Manifold) in order to process a multi-task for output according to the plurality of domains.

In other words, the MtLM according to an embodiment of the present disclosure not only simultaneously may learn knowledge data according to various domains, but also efficiently may learn relationships between multiple domains, thereby expanding the learning area and simultaneously performing effective multi-tasking learning that implements batch learning of local patterns according to each domain and common principles between the plurality of domains.

Accordingly, the MtLM may improve (or directly improve) the processing performance and accuracy of various multi-tasking tasks based on the model trained as above.

The MtLM may perform pre-training based on predetermined experimental data.

Herein, the experimental data according to an embodiment of the present disclosure may be data including predetermined material unique characteristic information and material physical property specific information as learning data used for training the MtLM.

In this case, the material unique characteristic information according to an embodiment of the present disclosure may be information that specifies the unique characteristics possessed by a predetermined material.

For example, the material unique characteristic information may include a predetermined material name, molecular structural formula, and/or chemical formula.

In addition, the material physical property specific information according to an embodiment of the present disclosure may specify the data value that a predetermined material has for a predetermined material property.

For example, the material physical property specific information may include material property (in other words, domain) values such as boiling point, melting point, refractive index, solubility, viscosity, surface tension, density, strength, and/or thermal conductivity of a predetermined material.

The MtLM that performed pre-learning as described above in an embodiment may input predetermined material unique characteristic information and/or material physical property specific information, and output predicted data based on the input information and trained knowledge.

The MtLM may receive predetermined material unique characteristic information and output predicted material physical property specific information based on the received information and trained knowledge.

In another embodiment, the MtLM may receive predetermined material physical property specific information and output predicted material unique characteristic information based on the received information and trained knowledge.

In another embodiment, the MtLM may receive predetermined material unique characteristic information and material physical property specific information, and output optimal material unique characteristic information and material physical property characteristics information predicted based on the received information and trained knowledge.

Figure 6:
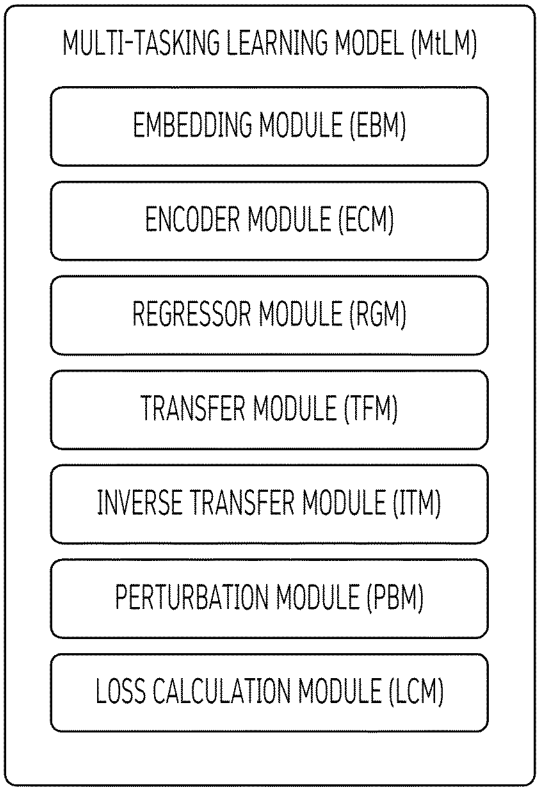
FIG. 6 is a schematic internal block diagram illustrating a multi-tasking learning model according to an embodiment of the present disclosure.

FIG. 6 is a schematic internal block diagram of the MtLM according to an embodiment of the present disclosure.

Referring to FIG. 6, in another aspect, the MtLM according to an embodiment of the present disclosure may include at least one of an embedding module (EBM), an encoder module (ECM), a regressor module (RGM), a transfer module (TFM), an inverse transfer module (ITM), a perturbation module (PBM), or a loss calculation module (LCM).

In detail, the EBM according to an embodiment of the present disclosure may be a pre-encoder module that transforms predetermined input data into an embedding vector.

In other words, the EBM may be a module that transforms specific input data into a vector format by projecting the same onto a predetermined embedding space.

The EBM may provide an embedding vector for input data based on a directed message passing neural network (DMPNN) structure.

In addition, the ECM according to an embodiment of the present disclosure may be a module that takes a predetermined embedding vector as input and transform the input embedding vector into a latent vector by projecting the same onto a latent space corresponding to the task.

In other words, the ECM may be a module that extracts the main features of the input embedding vector and expresses the same on the corresponding latent space.

The ECM may include a plurality of ECMs corresponding to each of the plurality of domains.

The ECM may include a first ECM corresponding to a first domain (for example, boiling point) and a second ECM corresponding to a second domain (for example, melting point).

In an embodiment, one of the plurality of ECMs may be a source ECM corresponding to a source task of transfer learning according to an embodiment of the present disclosure.

In addition, any one of the remaining ECMs excluding the source ECM may be a target ECM corresponding to a target task of transfer learning according to an embodiment of the present disclosure.

In addition, the RGM according to an embodiment of the present disclosure may be a head module that takes a predetermined latent vector as input and generates a final prediction value according to the input latent vector.

The RGM may be involved (or directly involved) in generating the final output and thus determine the prediction performance of a model.

In addition, the RGM may include a plurality of RGMs corresponding to each of the plurality of domains.

The RGM may include a first RGM corresponding to a first domain (for example, boiling point) and a second RGM corresponding to a second domain (for example, melting point).

In an embodiment, one of the plurality of RGMs may be a source RGM, which is the RGM corresponding to a source task of transfer learning according to an embodiment of the present disclosure.

In addition, any one of the remaining RGMs excluding the source RGM may be a target RGM corresponding to a target task of transfer learning according to an embodiment of the present disclosure.

In addition, the TFM according to an embodiment of the present disclosure may be a module that transforms a predetermined latent vector into a transfer vector by mapping the same to a latent space of another task.

In detail, the TFM may transform a specific latent vector into a transfer vector by mapping the same to the latent space of another task based on Riemannian geometry.

In this process, the TFM may implement the geometric alignment between each mapped task according to an embodiment of the present disclosure. A detailed explanation thereof is provided later in the multi-tasking model training method.

In other words, the TFM may effectively perform the transfer of knowledge data between a plurality of tasks by mapping the latent vector according to a first task to the latent space according to a second task through the geometric alignment according to an embodiment of the present disclosure.

The TFM may support data processing that improves the accuracy and consistency of the transformed vector (in other words, the transfer vector) by utilizing an autoencoder structure.

In addition, the TFM may include a plurality of TFMs corresponding to each of the plurality of domains.

The TFM may include a first TFM corresponding to a first domain (for example, boiling point) and a second TFM corresponding to a second domain (for example, melting point).

In an embodiment, one of the plurality of TFMs may be a source TFM, which is the TFM corresponding to a source task of transfer learning according to an embodiment of the present disclosure.

In addition, any one of the remaining TFMs excluding the source TFM may be a target TFM, which is the TFM corresponding to a target task of transfer learning according to an embodiment of the present disclosure.

In addition, the ITM according to an embodiment of the present disclosure may be a module that reconstructs a transfer vector mapped and transformed into a latent space of another task by the TFM so as to be mapped back to the original latent space.

Thus, the ITM may generate a vector (hereinafter, an inverse vector) that reconstructs and transforms a transfer vector back to its original state.

The ITM may improve the stability of the aforementioned reconstruction process and the accuracy and consistency of the corresponding transfer vector by utilizing the autoencoder structure.

The ITM may include a plurality of ITMs corresponding to each of the plurality of domains.

The ITM may include a first ITM corresponding to a first domain (for example, boiling point) and a second ITM corresponding to a second domain (for example, melting point).

In an embodiment, one of the plurality of ITMs may be a source ITM, which the ITM corresponding to a source task of transfer learning according to an embodiment of the present disclosure.

In addition, any one of the remaining ITMs excluding the source ITM may be a target ITM corresponding to a target task of transfer learning according to an embodiment of the present disclosure.

In addition, the PBM according to an embodiment of the present disclosure may be a module that generates a plurality of perturbation vectors by applying a predetermined change to a predetermined embedding vector.

In detail, the PBM may be a module that generates a plurality of perturbation vectors (in other words, perturbation points) on the periphery based on a specific embedding vector by applying a change that moves the corresponding embedding vector in a predetermined direction.

In this case, the plurality of generated perturbation vectors are designed to maintain a relative distance from the corresponding embedding vector, thereby effectively assisting the geometric alignment.

In other words, the aforementioned PBM may help align the coordinate systems between a source task and a target task by generating the plurality of perturbation vectors to assist in the geometric alignment of the model.

In addition, the PBM may compute the distance between a predetermined embedding vector and the plurality of perturbation vectors generated based thereon, and support matching the displacement between the source task and the target task based on the computed distance.

This may allow the PBM to more easily maintain consistency in the latent space for the model.

According to an embodiment of the present disclosure, the PBM may prevent overfitting of the model and improve generalization performance by forcing a relationship between a predetermined embedding vector and the plurality of perturbation vectors generated based thereon to be maintained.

In addition, the LCM according to an embodiment of the present disclosure may be a module that calculates various loss functions based on various vectors obtained through the MtLM.

The LCM may compute regression loss, autoencoder loss, consistency loss, mapping loss, distance loss, and/or integrated loss according to an embodiment of the present disclosure. A detailed explanation thereof is provided later in the multi-tasking model training method.

This may allow the LCM to support regularization and learning for different portions of the model, and to provide feedback for model learning, enabling model optimization.

In an embodiment, the MtLM may perform model optimization and update through various data processing processes linked with the modules described above.

For example, the MtLM may perform model optimization and parameter update in conjunction with the modules described above based on an AdamW optimization algorithm.

As such, the MtLM may simultaneously learn knowledge data according to various domains, and also efficiently learn relationships between multiple domains, thereby expanding the learning area and simultaneously performing effective multi-tasking learning that implements batch learning of local patterns according to each domain and common principles between the plurality of domains.

Accordingly, the MtLM may improve (or directly improve) the processing performance and accuracy of various multi-tasking tasks based on the model trained as above.

[Method for Implementing Multi-Tasking Learning Model Provision Service]

Hereinafter, a method for implementing the MtLM provision service that mutually transfers and learns knowledge data of a latent space for each task through the geometric alignment in one integrated latent space in order to process a multi-task for output according to a plurality of domains and performs multi-tasking based thereon by a computing system 1000 according to an embodiment of the present disclosure may be described in detail.

In general, existing transfer learning techniques may be mainly focused on classification tasks of image and/or language data sets, and have limitations in addressing regression problems or problems in non-Euclidean spaces.

In particular, when the training data set is insufficient, the decline in prediction performance for the aforementioned problems may be more inevitable, and when multi-tasking considering various task types is required, the decline in performance may be aggravated in learning and prediction therefor.

In addition, most existing methods may be optimized for handling data in Euclidean space, and thus may not operate effectively in complex curved spaces or nonlinear spaces.

Figure 7:
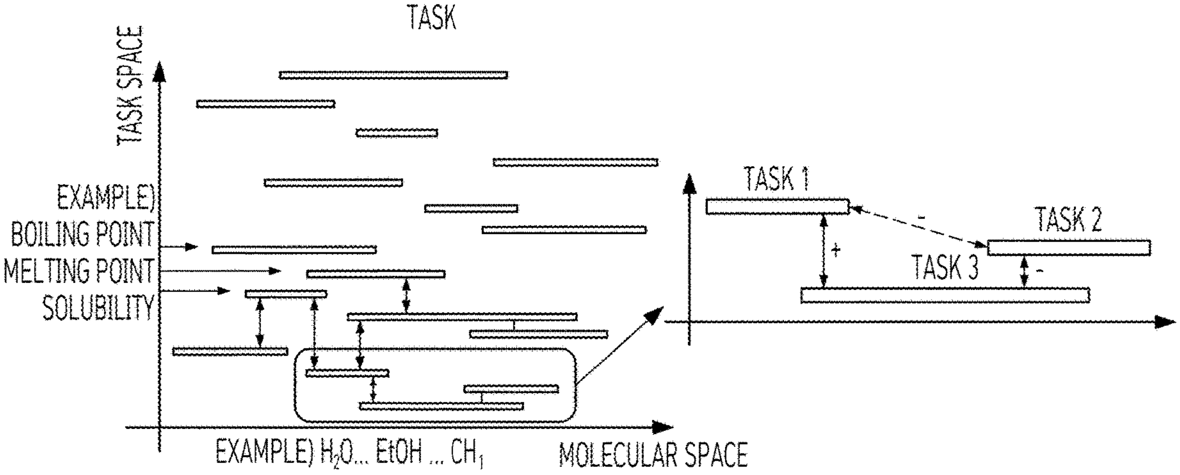
FIG. 7 is a schematic example conceptual diagram illustrating a multi-tasking model training method according to an embodiment of the present disclosure.

FIG. 7 is a schematic example conceptual illustrating a multi-tasking model training method according to an embodiment of the present disclosure.

Accordingly, as shown in FIG. 7, the computing system 1000 according to an embodiment of the present disclosure may provide a new multi-tasking model training method that may overcome the regression problem of a small data set and the limitations of existing transfer learning techniques, and a multi-tasking performing method using a machine learning model trained based thereon.

Hereinafter, in the description according to an embodiment of the present disclosure, for the sake of effective description, the material described above may be limited to a "molecule" and the domain thereof is described based on a "material property."

This may be because molecular data sets typically have small amounts of data, contain diverse task types, and primarily deal with regression problems.

In other words, in the case of molecular data sets, various task processing linked to numerous material properties may be required, but the data given therefor may be very limited, and each material property may have the characteristic of being closely associated with or influencing each other.

The molecular data set may be advantageously applicable to multi-task processing across the plurality of domains, and may be a desirable example for explaining the multi-tasking model training method and the multi-tasking performing method using the machine learning model trained based thereon according to an embodiment of the present disclosure.

However, it is not limited thereto, and it is obvious that any embodiment that may apply multi-tasks according to the plurality of domains may be included in an embodiment.

Hereinafter, the multi-tasking model training method and the multi-tasking performing method using the machine learning model trained based thereon according to an embodiment of the present disclosure will be described in more detail with reference to the attached drawings.

Figure 8:
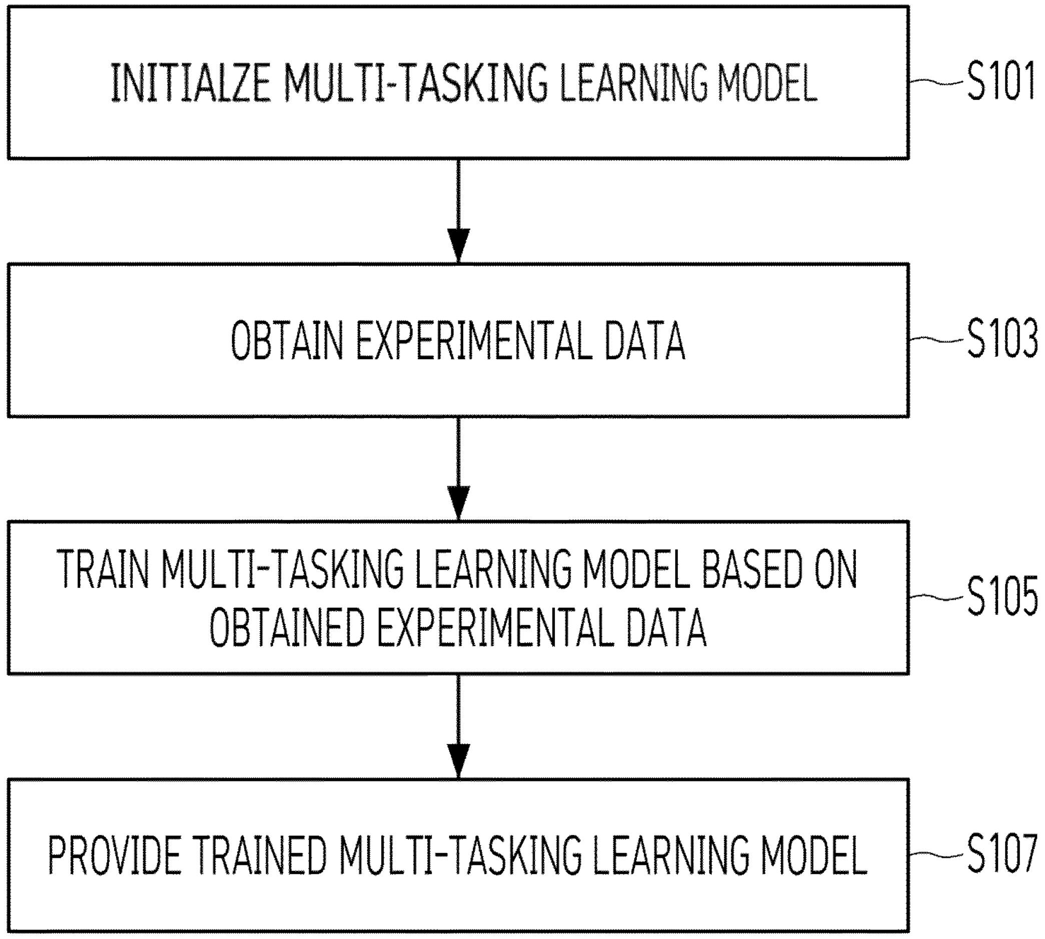
FIG. 8 is a schematic block flow diagram illustrating a multi-tasking model training method according to an embodiment of the present disclosure.

FIG. 8 is a schematic block flow illustrating a multi-tasking model training method according to an embodiment of the present disclosure.

Referring to FIG. 8, the multi-tasking model training method and the multi-tasking performing method using the machine learning model trained based thereon according to an embodiment of the present disclosure may include: initializing the MtLM (S101); obtaining experimental data (S103); training the MtLM based on the obtained experimental data (S105); and providing the trained MtLM (S107).

In detail, the computing system 1000 according to an embodiment of the present disclosure may initialize the MtLM (S101).

Herein, in other words, the MtLM (geometrically aligned transfer encoder model) according to an embodiment of the present disclosure may be a machine learning model that mutually aligns fragmented knowledge data (a latent vector) in a latent space for each task through geometric transfer in one integrated latent space (M) in order to process a multi-task for output according to the plurality of domains.

In other words, the MtLM according to an embodiment of the present disclosure simultaneously learns knowledge data according to various domains, and efficiently learn relationships between multiple domains, thereby expanding the learning area and simultaneously performing effective multi-tasking learning that implements batch learning of local patterns according to each domain and common principles between the plurality of domains.

In detail, the computing system 1000 may perform initialization for each component included in the MtLM as described above.

The computing system 1000 may initialize an embedding network (embedd ($x$)), an encoder network ($f_\epsilon$), a regressor (head) network ($f_h$), a transfer network ($f_t$), and/or an inverse network ($f_i$) within the MtLM with random parameters (θ).

In addition, the computing system 1000 may set up a predetermined optimization algorithm to be applied to the MtLM.

For example, the computing system 1000 may set up an AdamW (decoupled weight decay regularization) algorithm as the optimization algorithm, and according to an embodiment of the present disclosure, the optimization algorithm may be improved and used to independently process weight decay.

In addition, the computing system 1000 according to an embodiment of the present disclosure may obtain the experimental data (S103).

Herein, the experimental data according to an embodiment of the present disclosure ($x$) may be data including predetermined material unique characteristic information and material physical property specific information as learning data used for training the MtLM.

In this case, the material unique characteristic information according to an embodiment of the present disclosure may be information that specifies the unique characteristics possessed by a predetermined material. In other words, the material unique characteristic information may be information that specifies the unique characteristics possessed by a predetermined molecule.

For example, the material unique characteristic information may include a predetermined material name, molecular structural formula, and/or chemical formula.

In addition, the material physical property specific information according to an embodiment of the present disclosure may be information that specifies the data value that a predetermined material has for a predetermined material property.

For example, the material physical property specific information may include material property (in other words, domain) values such as boiling point, melting point, refractive index, solubility, viscosity, surface tension, density, strength, and/or thermal conductivity of a predetermined material.

In detail, the computing system 1000 may obtain the experimental data as described above based on predetermined user input and/or connection with an external server.

In addition, the computing system 1000 according to an embodiment of the present disclosure may train the MtLM based on the obtained experimental data (S105). Furthermore, the computing system 1000 according to an embodiment of the present disclosure may also provide the trained MtLM (S107).

Figure 9:
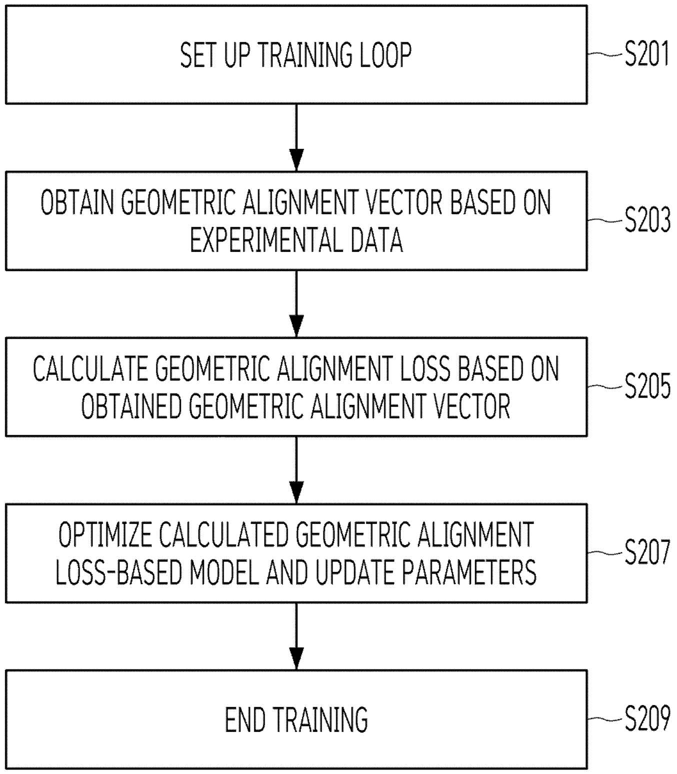
FIG. 9 is a schematic block flow diagram illustrating a multi-tasking learning model training method according to an embodiment of the present disclosure.
Figure 10:
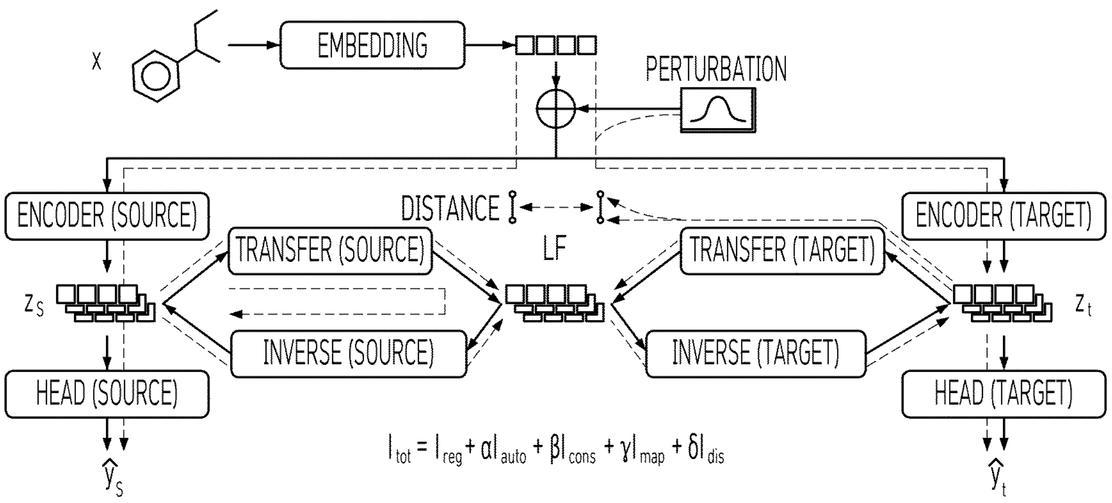
FIG. 10 is a schematic example conceptual diagram illustrating a multi-tasking learning model training method according to an embodiment of the present disclosure.

FIG. 9 is a schematic block flow illustrating a MtLM training method according to an embodiment of the present disclosure. FIG. 10 is a schematic example conceptual illustrating a MtLM training method according to an embodiment of the present disclosure.

In other words, referring to FIGS. 9 and 10, the computing system 1000 may perform pre-learning for the MtLM based on the experimental data obtained as described above.

In detail, the computing system 1000 may set up a training loop for the MtLM (S201).

In more detail, the computing system 1000 may set up the number of epoch repetitions, the number of task repetitions, and/or the number of batch repetitions during training.

The computing system 1000 may set up the training loop to repeatedly perform epoch "i" "from 1 to n (n>=1),"

repeatedly perform the same for each task "t," and repeatedly perform the same for each preset batch "b" during training.

In addition, the computing system 1000 may obtain a geometric alignment vector based on the experimental data obtained as described above (S203).

Herein, the geometric alignment vector according to an embodiment of the present disclosure may mean various vectors obtained through the MtLM.

The geometric alignment vector may include an embedding vector ($a$), a perturbation vector ($\{\bar{a}\}$), an encoding vector, a transfer vector, and an inverse vector.

In detail, the computing system 1000 may input the obtained experimental data into the MtLM.

In addition, firstly, the computing system 1000 may obtain an embedding vector based on the MtLM that inputs the experimental data.

In more detail, the computing system 1000 may transform the input experimental data into the embedding vector through an embedding network in conjunction with the EBM of the MtLM.

Accordingly, the computing system 1000 may obtain the embedding vector transformed into a vector format by projecting the experimental data into a predetermined embedding space.

In addition, secondly, the computing system 1000 may generate a perturbation vector based on the obtained embedding vector.

In detail, the computing system 1000 may generate a plurality of perturbation vectors (in other words, perturbation points) on a predetermined periphery based on the obtained embedding vector in conjunction with the PBM of the MtLM.

The computing system 1000 may repeatedly perform the aforementioned functional operation for each task to obtain the corresponding perturbation vector for each task.

The computing system 1000 may obtain a perturbation vector corresponding to task "t" and a perturbation vector corresponding to task "s."

In addition, thirdly, the computing system 1000 may obtain an encoding vector based on the generated perturbation vector and embedding vector.

Herein, the encoding vector according to an embodiment of the present disclosure may include a perturbation latent vector, which is a latent vector generated based on a predetermined perturbation vector, and an original latent vector generated based on an embedding vector, which is an original vector of the perturbation vector.

In detail, the computing system 1000 may transform the generated perturbation vector into a latent vector by projecting the same into a latent space corresponding to the task through an encoder network in conjunction with the encoder module of the MtLM.

In addition, the computing system 1000 may transform the obtained embedding vector into a latent vector by projecting the same into a latent space corresponding to the task through an encoder network in conjunction with the encoder module of the MtLM.

Thus, the computing system 1000 may obtain a perturbation latent vector and an original latent vector.

The computing system 1000 may repeatedly perform the aforementioned functional operation for each task to obtain the corresponding original latent vector and perturbation latent vector for each task.

The computing system 1000 may obtain an original latent vector ($z_t$: hereinafter, t original latent vector) corresponding to the task "t" and a perturbation latent vector ($\{\bar{z}_t\}$: hereinafter, t perturbation latent vector) corresponding to the task "t."

In addition, the computing system 1000 may obtain an original latent vector ($z_s$: hereinafter, s original latent vector) corresponding to the task "s" and a perturbation latent vector ($\{\bar{z}_s\}$: hereinafter, s perturbation latent vector) corresponding to the task "s."

In addition, fourthly, the computing system 1000 may obtain a transfer vector based on the obtained encoding vector.

Herein, the transfer vector according to an embodiment of the present disclosure may include a perturbation transfer vector, which is a transfer vector generated based on a predetermined perturbation latent vector, and an original transfer vector, which is a transfer vector generated based on an original latent vector corresponding to the perturbation latent vector.

In detail, the computing system 1000 may transform the obtained perturbation latent vector and original latent vector into a transfer vector by mapping the same to the latent space of another task (the task "s" or the task "t") through the transfer network in conjunction with the TFM of the MtLM.

Thus, the computing system 1000 may obtain a perturbation transfer vector and an original transfer vector.

The computing system 1000 may repeatedly perform the aforementioned functional operation for each task to obtain the corresponding original transfer vector and perturbation transfer vector for each task.

The computing system 1000 may obtain an original transfer vector ($m_t$: hereinafter, t original transfer vector) corresponding to the task "t" and a perturbation transfer vector ($\{\bar{m}_t\}$: hereinafter, t perturbation transfer vector) corresponding to the task "t."

In addition, the computing system 1000 may obtain an original transfer vector ($m_s$: hereinafter, s original transfer vector) corresponding to the task "s" and a perturbation transfer vector ($\{\bar{m}_s\}$: hereinafter, s perturbation transfer vector) corresponding to the task "s."

Thus, the computing system 1000 may obtain geometric alignment vectors (in other words, the embedding vector, perturbation vector, encoding vector (including the original latent vector and the perturbation latent vector), and transfer vectors (including the original transfer vector and the perturbation transfer vector)) based on the experimental data.

In addition, fifthly, the computing system 1000 may obtain an inverse vector based on the obtained transfer vector.

Herein, the inverse vector according to an embodiment of the present disclosure may include a perturbation inverse vector, which is an inverse vector generated based on a predetermined perturbation transfer vector, and an original inverse vector, which is an inverse vector generated based on the original transfer vector corresponding to the perturbation transfer vector.

In detail, the computing system 1000 may reconstruct the obtained perturbation transfer vector and original transfer vector through the inverse network so as to be mapped back to the original latent space and transformed into the inverse vector in conjunction with the ITM of the MtLM.

Thus, the computing system 1000 may obtain the perturbation inverse vector and the original inverse vector.

The computing system 1000 may repeatedly perform the aforementioned functional operation for each task to obtain the corresponding original inverse vector and perturbation inverse vector for each task.

The computing system 1000 may obtain an original inverse vector ($\hat{z}_t$: hereinafter, t original inverse vector) corresponding to the task "t" and a perturbation inverse vector ($z'_t$:

hereinafter, t perturbation inverse vector) corresponding to the task "t."

In addition, the computing system 1000 may obtain an original inverse vector ($\hat{z}_s$: hereinafter, s original inverse vector) corresponding to the task "s" and a perturbation inverse vector ($z'_s$:

hereinafter, s perturbation inverse vector) corresponding to the task "s."

Thus, the computing system 1000 may obtain geometric alignment vectors (in other words, the embedding vector, perturbation vector, encoding vector (including the original latent vector and the perturbation latent vector), transfer vectors (including the original transfer vector and the perturbation transfer vector), and inverse vectors (including the original inverse vector and the perturbation inverse vector)) based on experimental data.

In addition, the computing system 1000 may calculate geometric alignment loss based on the obtained geometric alignment vector (S205).

Herein, the geometric alignment loss according to an embodiment of the present disclosure may mean various loss functions (Loss) computed based on various vectors (in other words, geometric alignment vectors) obtained through the MtLM.

The geometric alignment loss may include a regression loss ($L_{reg}$), an autoencoder loss ($L_{auto}$), a consistency loss ($L_{cons}$), a mapping loss ($L_{map}$) a distance loss ($L_{dis}$), and/or an integrated loss ($L_{tot}$).

In the following description, for the sake of effective explanation, the geometric alignment loss may be calculated based on the task "t."

Figure 11:
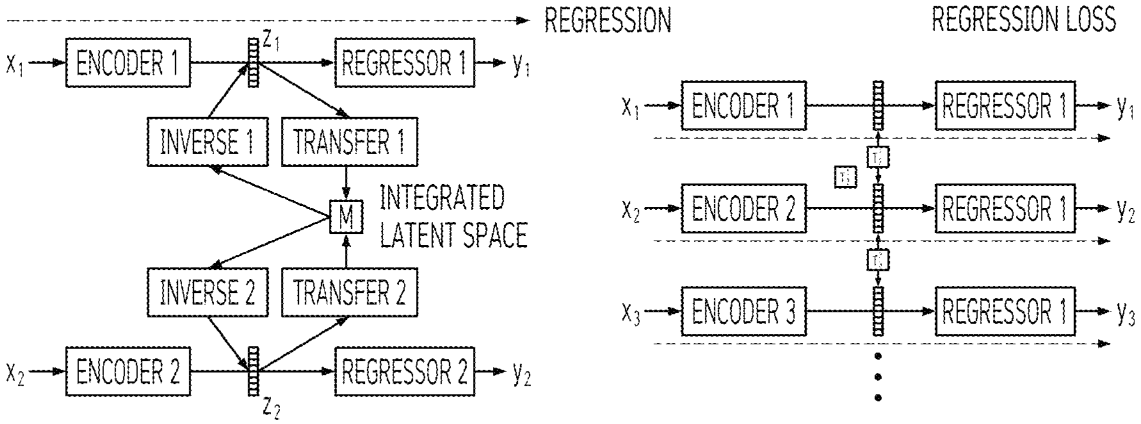
FIGS. 11 and 12 are schematic example diagrams illustrating a method for computing regression loss according to an embodiment of the present disclosure.
Figure 12:
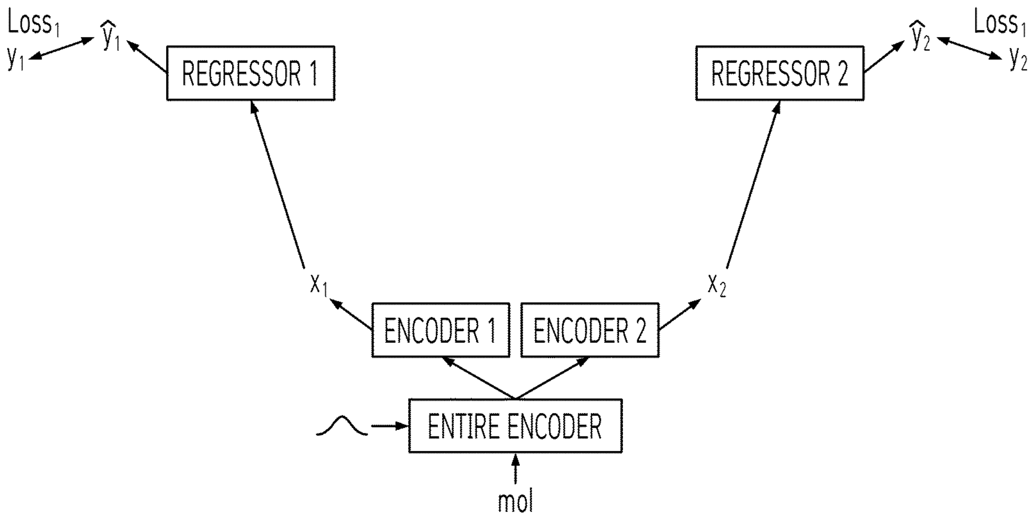

FIGS. 11 and 12 are schematic example illustrating a method for computing regression loss according to an embodiment of the present disclosure.

In detail, referring to FIGS. 10, 11, and 12, firstly, the computing system 1000 may compute a regression loss based on the MtLM that has obtained the geometric alignment vector.

In more detail, the computing system 1000 may calculate a regression loss based on a prediction value ($\hat{y}_t$) and an actual value ($y_t$, in other words, label value) predicted through the RGM according to [Equation 1] below. Herein, the prediction value of [Equation 1] may also be expressed as "$f_h(z_t)$."

$$L_{reg} = MSE(\hat{y}_t, y_t) \quad \text{[Equation 1]}$$

In other words, the computing system 1000 may compute the regression loss by calculating a mean squared error (MSE) between the prediction value and the actual value.

In an embodiment, each task may prevent mutual interference by computing an independent regression loss based on the ECM and the RGM matching each task and performing learning based thereon.

As such, the computing system 1000 may easily evaluate the regression performance of the model by computing the regression loss.

In addition, referring further to FIG. 10, secondly, the computing system 1000 may compute the autoencoder loss based on the MtLM that has obtained the geometric alignment vector.

In detail, the computing system 1000 may compute the autoencoder loss based on the original latent vector and the original inverse vector according to [Equation 2] below.

$$L_{auto} = MSE(\hat{z}_t, z_t) \quad \text{[Equation 2]}$$

In other words, the computing system 1000 may compute the autoencoder loss by calculating the MSE between the latent vector and the inverse vector.

The computing system 1000 may improve accuracy in the data transfer process through the autoencoder loss computed as above.

Figure 13:
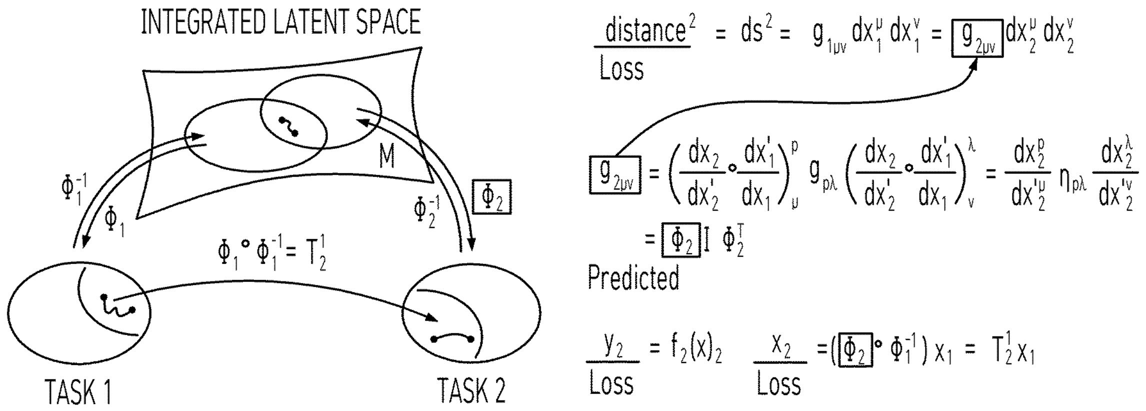
FIG. 13 is a schematic example diagram illustrating an integrated latent space mapping method according to an embodiment of the present disclosure.

FIG. 13 is a schematic example illustrating an integrated latent space (M) mapping method according to an embodiment of the present disclosure.

Referring to FIG. 13, the computing system 1000 may learn a bidirectional transformation matrix (TM) that may be mapped to a common integrated latent space (M) for each task.

In detail, the computing system 1000 may connect latent spaces between tasks by utilizing knowledge data that contain labels for both tasks.

In this process, the computing system 1000 may compute consistency loss and mapping loss according to an embodiment of the present disclosure.

Figure 14:
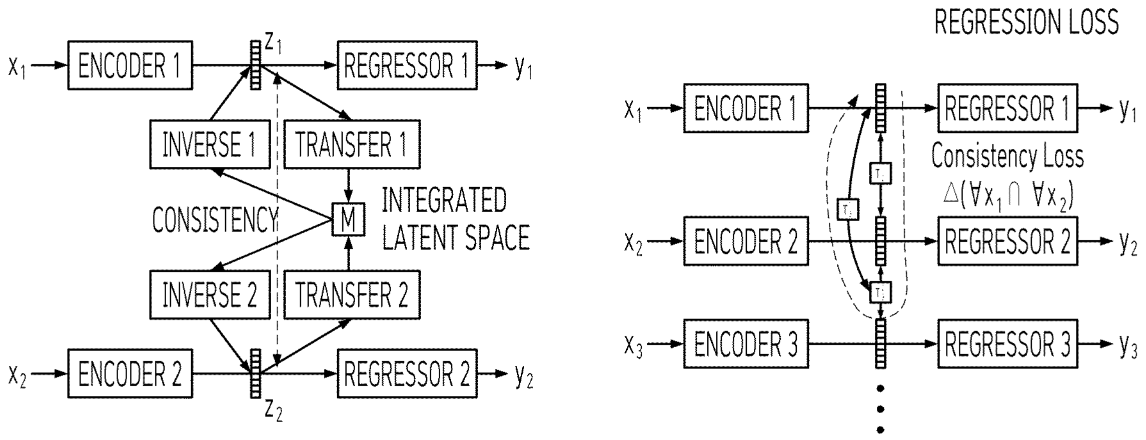
FIGS. 14 and 15 are schematic example diagrams illustrating a consistency loss computation method according to an embodiment of the present disclosure.
Figure 15:
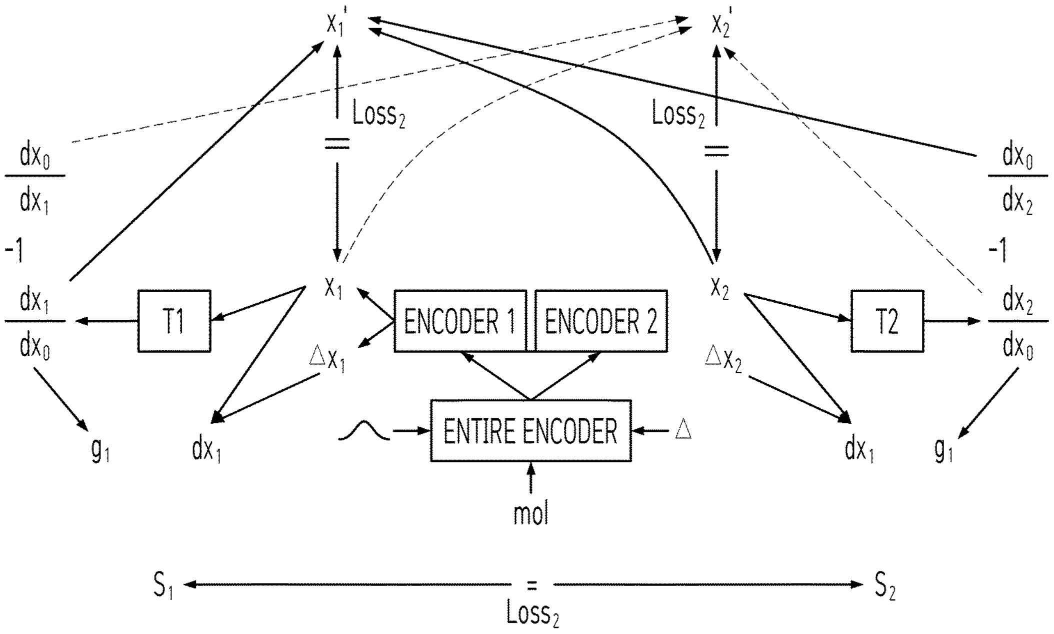

FIGS. 14 and 15 are schematic example illustrating a consistency loss computation method according to an embodiment of the present disclosure.

In more detail, referring to FIGS. 10, 14 and 15, thirdly, the computing system 1000 may compute consistency loss based on the MtLM that has obtained the geometric alignment vector.

Particularly, the computing system 1000 may compute the consistency loss based on the perturbation transfer vector of the task "t" and the perturbation transfer vector of the task "s" according to [Equation 3] below.

$$L_{cons} = MSE(\{\overline{m}_s\}, \{\overline{m}_t\}) \quad \text{[Equation 3]}$$

In other words, the computing system 1000 may compute the consistency loss by calculating the MSE between the t perturbation transfer vector and the s perturbation transfer vector.

The computing system 1000 may derive a metric for calculating a distance in space from a transformation matrix (TM), and learn to make the distance in the latent space of each task the same based on the derived metric.

Thus, the computing system 1000 may more effectively implement the geometric alignment between tasks.

Figure 16:
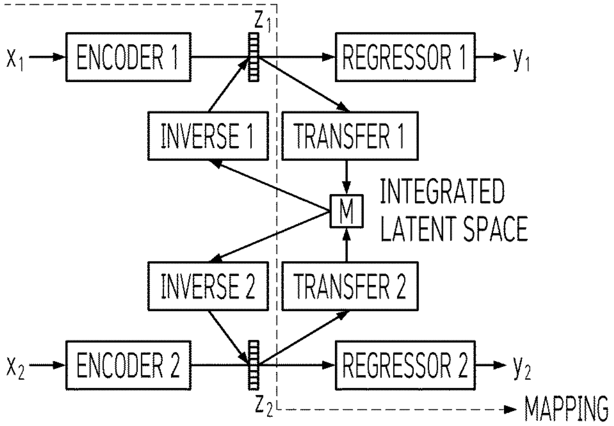
FIGS. 16 and 17 are schematic example diagrams illustrating a mapping loss computation method according to an embodiment of the present disclosure.
Figure 16:
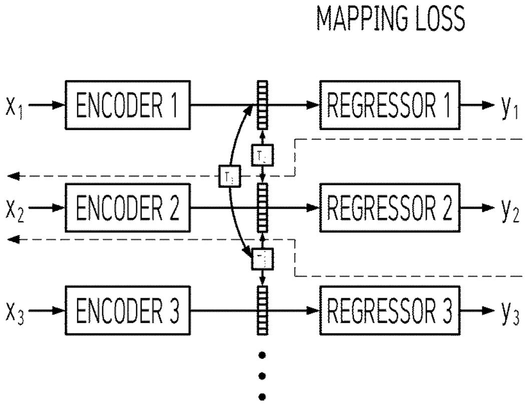
Figure 17:
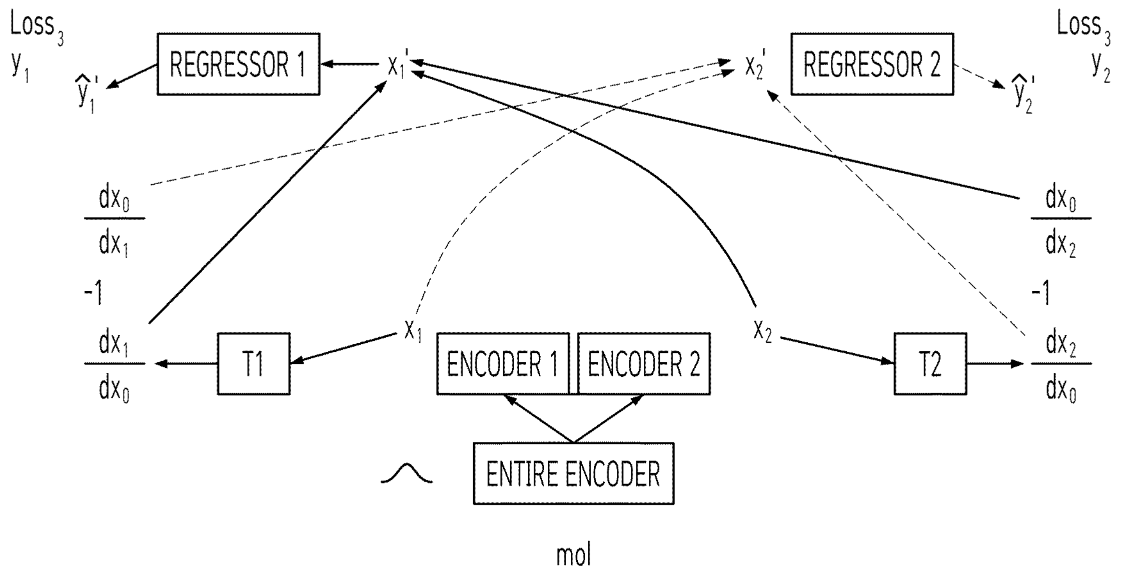

FIGS. 16 and 17 are schematic example illustrating a mapping loss computation method according to an embodiment of the present disclosure.

In addition, referring to FIGS. 10, 16 and 17, fourthly, the computing system 1000 may compute a mapping loss based on the MtLM that has obtained the geometric alignment vector.

In detail, the computing system 1000 may compute the mapping loss based on a prediction value based on an actual value according to the task "t" and an original inverse vector according to the task "s" according to [Equation 4] below.

$$L_{map} = MSE(f_h(f_t(m_s)), y_t) \quad \text{[Equation 4]}$$

In other words, the computing system 1000 may compute the mapping loss by calculating the MSE between the actual value of the task "t" and the prediction value according to the original inverse vector of the task "s."

The computing system 1000 may implement learning to transfer latent vectors from the latent space of one task to the latent space of the other task by computing the mapping loss as described above, and perform the other task based on the transferred vectors, thereby inducing latent characteristics to become similar to each other.

Thus, the computing system 1000 may evaluate the prediction performance of vectors transferred to the latent space of other tasks and induce learning in a direction to improve the same.

In addition, referring further to FIG. 10, fifthly, the computing system 1000 may compute a distance loss based on the MtLM that has obtained the geometric alignment vector.

In detail, the computing system 1000 may compute the distance loss between tasks based on the distance between the original transfer vector and the perturbation transfer vector of each task ($S_i$: hereinafter, transfer vector displacement) according to [Equation 5] and [Equation 6] below.

In more detail, the computing system 1000 may calculate the distance $(s_i^t$:

hereinafter, t transfer vector displacement) between the t original transfer vector and the t perturbation transfer vector according to the task "t" according to [(a) of Equation 5] below.

In addition, the computing system 1000 may calculate the distance $(s_i^s$:

hereinafter, s transfer vector displacement) between the s original transfer vector and the s perturbation transfer vector according to the task "s" according to [(b) of Equation 5] below.

$$s_i^s = m_t - \{\overline{m}_t\} \ (a) \quad \text{[Equation 5]}$$

$$s_i^t = m_s - \{\overline{m}_s\} \ (b)$$

In addition, the computing system 1000 may compute the MSE between the t transfer vector displacement and the s transfer vector displacement according to [Equation 6] below to compute the distance loss.

$$L_{dis} = \frac{1}{M}\sum_i MSE(s_i^s, s_i^t) \quad \text{[Equation 6]}$$

Herein, the "M" in [Equation 6] may mean the number of perturbation points.

The computing system 1000 may define the t transfer vector displacement and the transfer vector displacement as displacements in the source task and the target task, respectively.

Thus, the computing system 1000 may calculate the distance between the original transfer vector and the perturbation transfer vector by interpreting the "t transfer vector displacement" and the "s transfer vector displacement" as being in a flat Euclidean space.

Accordingly, the computing system 1000 may support more complete consistency maintenance of the latent space of the model.

Figure 18:
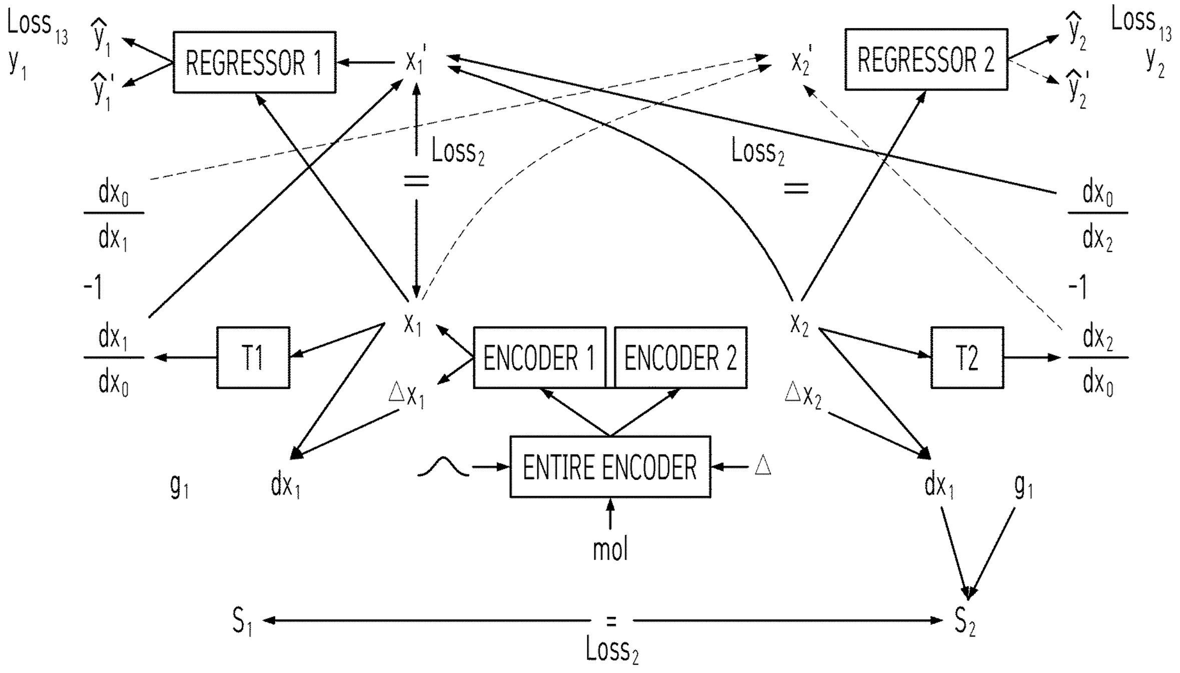
FIG. 18 is a schematic example diagram illustrating an integrated loss computation method according to an embodiment of the present disclosure.

FIG. 18 is a schematic example illustrating an integrated loss computation method according to an embodiment of the present disclosure.

In addition, referring to FIGS. 10 and 18, sixthly, the computing system 1000 may compute an integrated loss based on the MtLM that has obtained the geometric alignment vector.

In detail, the computing system 1000 may compute the integrated loss by weighted summing the regression loss, autoencoder loss, consistency loss, mapping loss, and distance loss described above according to [Equation 7] below.

$$L_{tot} = L_{reg} + \alpha L_{auto} + \beta L_{cons} + \gamma L_{map} + \delta L_{dis} \quad \text{[Equation 7]}$$

The computing system 1000 may apply weights to each loss function so that each loss function may be optimized for a specific aspect of the model.

Herein, in [Equation 7], the "α" is the weight of the autoencoder loss, the "β" is the weight of the consistency loss, the "γ" is the weight of the mapping loss, and the "δ" is the weight of the distance loss.

The computing system 1000 may update parameters in a direction to minimize the integrated loss by adjusting the importance of the loss function corresponding to each weight during the learning process of the model by utilizing the above weights.

Returning back to FIG. 9, in another embodiment, the computing system 1000 may also optimize calculated geometric alignment loss-based model and update parameters as described above (S207).

In detail, the computing system 1000 may perform optimization and parameter update for the MtLM based on the integrated loss described above.

The computing system 1000 may calculate a gradient based on the integrated loss for each parameter of the MtLM through backpropagation.

In addition, the computing system 1000 may perform parameter update of the MtLM using a calculated gradient and a preset optimization algorithm (for example, AdamW (decoupled weight decay regularization) algorithm).

Thus, the computing system 1000 may implement the MtLM optimization based on the geometric alignment loss (particularly, integrated loss).

As such, the computing system 1000 may perform the MtLM optimization and parameter update learning through a combination of multiple loss functions calculated in various ways.

In this case, each loss function may assist in improving the performance of the model by correcting the accuracy, consistency, and/or distance of the knowledge data mapping.

Thus, the computing system 1000 may implement a multi-tasking model that provides improved performance that overcomes the regression problem of a small data set and the limitations of existing transfer learning techniques, while operating and providing improved generalization performance.

In addition, the computing system 1000 may end (or complete) the MtLM training (S209).

In detail, the computing system 1000 may end (or complete) the MtLM training process described above when a preset training ending condition is met.

The computing system 1000 may end (or complete) the MtLM training upon completion of a set training loop.

In other words, the computing system 1000 may provide the MtLM trained as described above in a predetermined manner.

The computing system 1000 may provide the MtLM trained in conjunction with a predetermined application service (for example, a material synthesis/evaluation service, a material physical property prediction service, and/or an optimal material recommendation service).

Thus, the computing system 1000 may support processing of various multi-tasking tasks using the MtLM with improved performance.

As such, the computing system 1000 may provide the MtLM that provides improved performance that overcomes the regression problem of a small data set and the limitations of existing transfer learning techniques by mutually transferring and learning knowledge data of a latent space for each task through the geometric alignment in one integrated latent space in order to process a multi-task for output according to a plurality of domains, while operating more stably.

Thus, the computing system 1000 may provide a transfer learning-based multi-tasking model that operates with high generalization performance even in situations where the amount of given data is small, various task types are included, or regression problems are dealt with.

In other words, the computing system 1000 may provide the MtLM with improved prediction performance based on knowledge distilled through geometric alignment-based transfer learning performed in conjunction with other domains, even when there is a domain among the plurality of domains (in an embodiment, material properties) that lacks experimental data (learning data).

For example, the computing system 1000 pre-trains the MtLM based on the first, second, third, fourth, fifth, sixth, seventh, eighth, ninth, and tenth material properties for each of a plurality of molecular structural formulas Then, when a first molecular structural formula including only data for the first to fifth material properties is input, the computing system 1000 may predict data values for the remaining sixth, seventh, eighth, ninth, and tenth material properties for the first molecular structural formula based on the knowledge data transferred and distilled through pre-training, and generate and provide output data based thereon.

As such, the computing system 1000 according to an embodiment of the present disclosure may provide a multi-tasking model that implements effective transfer learning based on the geometric alignment, guarantee high generalization performance, improve prediction accuracy for regression problems, support regularization according to a combination of various loss functions, and perform a stable learning process to guarantee robust performance.

Hereinbefore, a multi-tasking model training method and a multi-tasking performing method using a machine learning model trained based thereon according to an embodiment of the present disclosure can provide a multi-tasking model that maintains high performance even in a small data set by addressing the issue of insufficient data by transferring knowledge trained in a source task to a target task through transfer learning.

Accordingly, the multi-tasking model training method and the multi-tasking performing method using the machine learning model trained based thereon according to an embodiment of the present disclosure may expand the scope of application to fields where it was difficult to apply the machine learning model due to insufficient data or domain knowledge.

In addition, the multi-tasking model training method and the multi-tasking performing method using the machine learning model trained based thereon according to an embodiment of the present disclosure may provide a specialized transfer learning technique that can be effectively applied to regression problems, thereby demonstrating high prediction performance even in complex regression problems such as molecular data sets.

In addition, the multi-tasking model training method and the multi-tasking performing method using the machine learning model trained based thereon according to an embodiment of the present disclosure may improve the efficiency of transfer learning by maintaining geometric consistency between tasks by optimizing knowledge transfer between source tasks and target tasks through a Riemannian geometric approach.

In addition, the multi-tasking model training method and the multi-tasking performing method using the machine learning model trained based thereon according to an embodiment of the present disclosure may further improve the generalization performance of the model by combining multiple loss functions to regularize various aspects of the model.

Accordingly, the multi-tasking model training method and the multi-tasking performing method using the machine learning model trained based thereon according to an embodiment of the present disclosure may provide a multi-tasking model that can be universally utilized for various materials (substances), thereby improving the quality of the related industry as a whole.

[Method for Predicting Characteristic of Plurality of Material Properties Regarding Specific Material]

Hereinafter, referring to FIGS. 19, 20, and 21, a method of training an integrated prediction model that predicts characteristics regarding a plurality of material properties regarding a material based on the multi-tasking model training method described above, and providing a service for predicting the material properties therethrough may be described.

Figure 19:
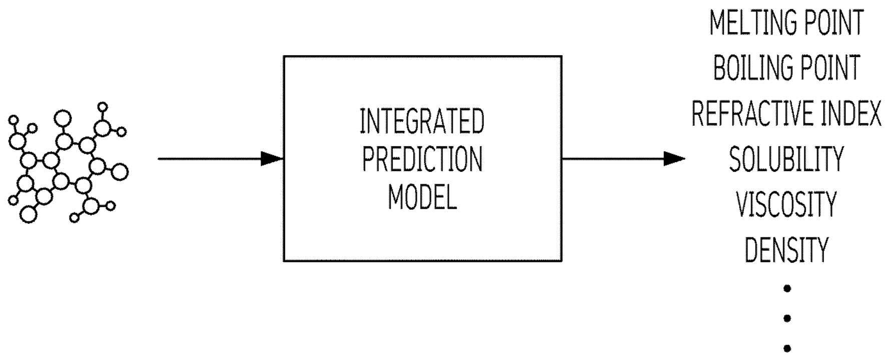
FIG. 19 is a schematic conceptual diagram illustrating an integrated prediction model capable of predicting a characteristic value for each of a plurality of material properties for a material according to an embodiment of the present disclosure.

Referring to FIG. 19, when inputting material property information (or material information) to be predicted as input data through the integrated prediction model, the computing system 1000 according to an embodiment of the present disclosure may predict a characteristic for each of the plurality of material properties regarding the input material property information (or material information) and provide the same as output data.

The integrated prediction model may be trained according to the training method of the multi-task learning model described above.

Accordingly, the integrated prediction model may be an integrated prediction model that is trained to output prediction values for each of the plurality of material properties regarding material information by training that the domains correspond to the material properties and the input data corresponds to the material information in the multi-tasking learning model capable of performing multiple tasks to predict outputs for input data in the plurality of domains for input data. For example, the material information, which is input data of the integrated prediction model, may be a 2-dimensional to n-dimensional molecular structural formula, and each task is designed to predict characteristic values for each material property for the molecular structural formula. Accordingly, the output data may be predicted characteristic values (herein, the values include a range) for each of the plurality of material properties for the input molecular structural formula.

The multi-tasking model training method described above learns about a relationship between material properties in the process of learning tasks that predict the plurality of material properties regarding the material information together. Hence, it is possible to learn not only the principles for the material information and individual material properties but also common principles for all trained material properties, thus enabling accurate prediction for each material property and easy updating.

In addition, the multi-tasking model training method may be able to learn about a wider range of materials because the learning data for the plurality of material properties include various materials, thereby expanding the range of predictable materials for each material property.

Accordingly, the integrated prediction model according to an embodiment of the present disclosure may be a multi-tasking model trained according to the aforementioned multi-tasking model training method configured to perform a first task for predicting a characteristic value of a first material property, a second task for predicting a characteristic value of a second material property, and an n-th task for predicting a characteristic value of an n-th material property for a molecular structural formula.

Accordingly, the computing system 1000 may input the first molecular structural formula into the integrated prediction model as input data, output the characteristic value of the n-th material property from the characteristic value of the first material property predicted for a material having the first molecular structural formula, and provide the output to a user.

Hereinafter, with reference to FIGS. 20 and 21, an integrated prediction model training method and prediction method for predicting a plurality of material properties of a material through the aforementioned multi-tasking model training method will be described. In this case, the method added to the aforementioned multi-tasking model training method to specialize in predicting the material properties is described in detail, and any redundant explanations are briefly explained or omitted.

Figure 20:
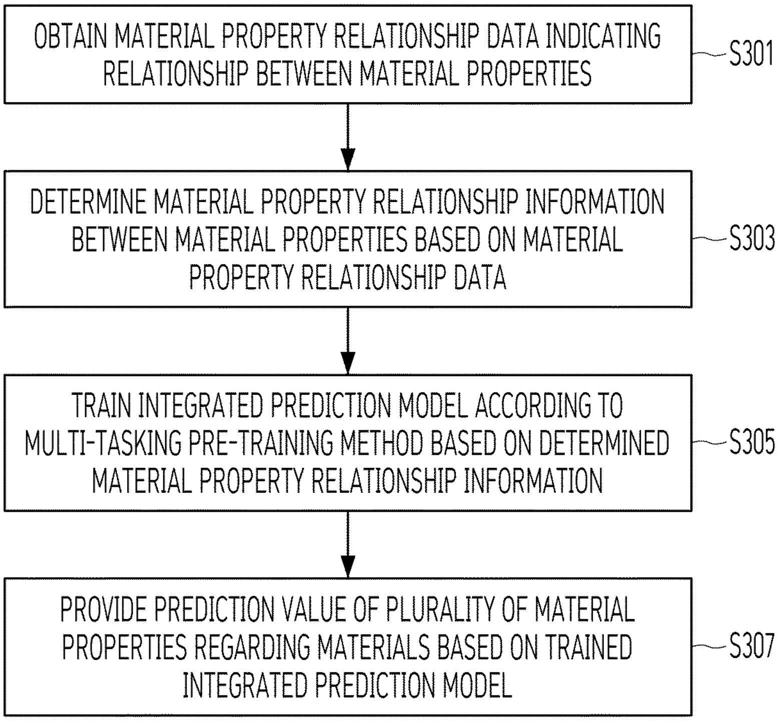
FIG. 20 is a schematic flowchart illustrating a method for predicting a characteristic for each of a plurality of material properties for a material by pre-training an integrated prediction model according to an embodiment of the present disclosure.

Referring to FIG. 20, in a method for predicting material properties using the integrated prediction model according to an embodiment of the present disclosure, the computing system 1000 may obtain material property relationship data indicating the relationship between material properties (S301).

In detail, a material property relationship data database included in the computing system 1000 may store data including information on the relationship between material properties.

The material property relationship data database may store data collected manually by people, and may also automatically search, extract, and edit data using pre-trained artificial intelligence models.

The computing system 1000 may perform a task of collecting and storing material property relationship data through prompt engineering for a pre-trained large-scale language model to increase reliability. In detail, the computing system 1000 may build a database of material property relationship data by searching a specialized data database (for example, theses, patents, or academic data) based on keywords about material properties through a large-scale language model, extracting information indicating material property relationships from the searched data, and classifying, characterizing and then organizing the extracted material property relationships by material property type or relationship type through an editing process.

Thereafter, the computing system 1000 may determine material property relationship information between material properties based on the material property relationship data (S303).

In detail, the computing system 1000 may determine the material property relationship information on a relationship between each different material properties based on the material property relationship data through a large-scale language model, and output the determined material property relationship information.

Figure 21:
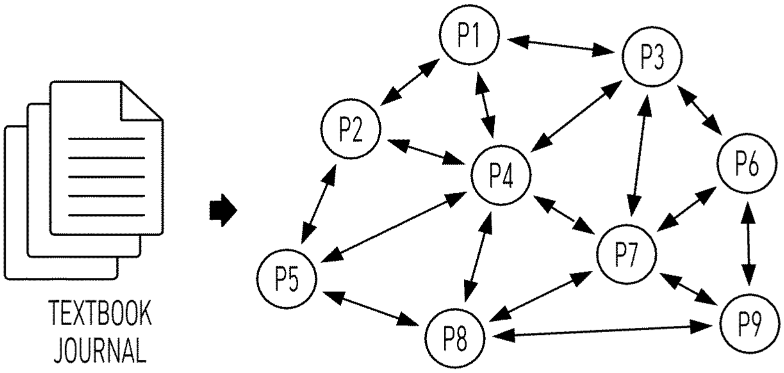
FIG. 21 is a schematic knowledge graph illustrating a relationship between material properties according to an embodiment of the present disclosure.
Figure 22:
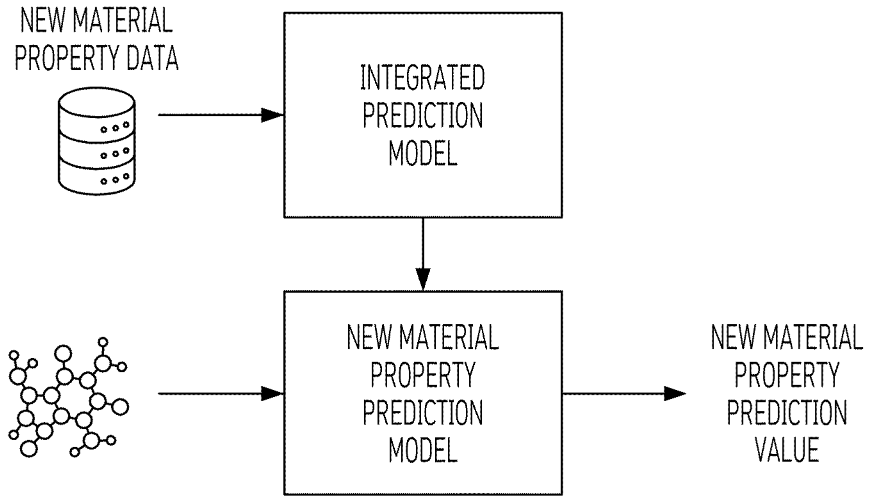
FIG. 22 illustrates a schematic process of generating a new prediction model from a pre-trained integrated prediction model according to an embodiment of the present disclosure.
Figure 23:
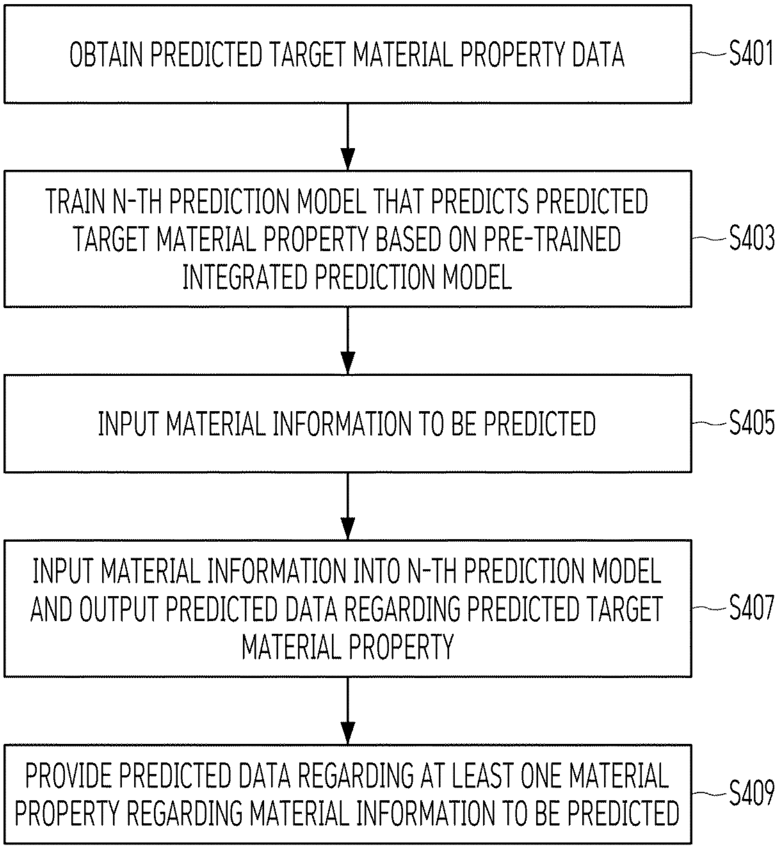
FIG. 23 is a schematic flowchart illustrating a method for updating a new task for predicting a new material property in a pre-trained integrated prediction model according to an embodiment of the present disclosure.

For example, referring to FIG. 21, a knowledge graph may be output with the material property relationship information, and may include relationship information between the first to n-th material properties to be integratedly learned, including relationship information between the first material property (P1) and the second material property (P2) and relationship information with the third material property (P3).

Particularly, the material property relationship information may include information on material properties associated with a specific property, information that determines the relationship characteristics such as trade-off, similarity, or correlation when associated, and information indicating the degree of association in the determined relationship characteristics.

For example, the material property relationship characteristics may include at least one of the relationship characteristics of trade-off relationship, similarity relationship, correlation, cause and effect relationship, independence relationship, proportional relationship, or inverse relationship.

The material property relationship characteristics and the degree of association may be divided into a numerical value indicating association in a positive correlation and a numerical value indicating association in a negative correlation, both of which may be represented as a knowledge graph.

Thereafter, the computing system 1000 may train the integrated prediction model according to multi-tasking pre-training method based on determining material property relationship information (S305) so that the material property relationship characteristic information is reflected in the weight of at least one of the aforementioned losses during the pre-training of the integrated prediction model, thereby reflecting the relationship information between the material properties of multiple material properties.

In an embodiment, when the relationship between the first material property and the second material property is expressed as a formula in the material property relationship data database, the computing system 1000 may detect the same.

When there is a formula representing the relationship between material properties, the computing system 1000 may secure more data sets by augmenting the data set for training the integrated prediction model.

For example, the computing system 1000 may apply a detected formula to a data set having only the first material property for a material to augment the same into a data set including the second material property, and vice versa.

In another embodiment, when there is a formula representing the relationship between material properties, the computing system 1000 may update the integrated prediction model to predict the second material property by applying the detected formula to the first material property when only the first material property is trained among the first and second material properties.

In yet another embodiment, when there is a formula representing the relationship between material properties, the computing system 1000 may perform transfer learning again according to the pre-training method of the multi-tasking model between the model of the task of predicting the first material property and the model of the task of predicting the second material property based on the formula when both tasks of predicting the first material property and the second material property are trained, thereby optimizing the integrated prediction model and improving the mapping of the integrated latent space.

Returning to the description of the pre-training method for the integrated prediction model, the computing system 1000 may simultaneously learn tasks for predicting at least two material properties according to the multi-tasking pre-training method (S305).

In detail, as described above, the computing system 1000 may simultaneously pre-learn the source task and the target task through transfer learning when the prediction for the first material property is referred to as the source task and the prediction for the second material property is referred to as the target task.

To this end, the computing system 1000 may obtain experimental data.

Herein, the experimental data is learning data used for training the integrated prediction model, and may be data including the material property specific information mapped to predetermined material unique characteristic information. Hereinafter, the material unique characteristic information may be explained by limiting the same to the molecular structural formula.

Particularly, the experimental data may include first experimental data including information on the first material property for the molecular structural formula of a plurality of materials, and second experimental data including information on the second material property for the molecular structural formula of the plurality of materials.

Herein, the plurality of materials of the first experimental data and the materials of the second experimental data may be different from each other, or at least some thereof may be the same.

In this case, when there is a formula representing the relationship between material properties, the computing system 1000 may secure more data sets by augmenting the data set for training the integrated prediction model.

Next, the computing system 1000 may train the integrated prediction model based on the obtained experimental data.

In detail, the computing system 1000 may set up a training loop for the integrated prediction model.

In addition, the computing system 1000 may obtain a geometric alignment vector based on the experimental data obtained as described above.

Particularly, the computing system 1000 may obtain an embedding vector for the molecular structural formula of the first experimental data, generate a perturbation vector based on the obtained embedding vector, and obtain an encoding vector based on the generated perturbation vector and embedding vector. Herein, the encoding vector may be an encoder for the source task. In addition, the computing system 1000 may obtain a transfer vector based on the obtained encoding vector. In detail, the encoding vector may be transferred to the integrated latent space through the TFM of the source task to obtain the transfer vector. The transfer learning may be performed by obtaining an inverse vector based on the obtained transfer vector through the TFM of the target task. The specific derivation process for each stage may be replaced by the explanation described above.

Next, the computing system 1000 may calculate a geometric alignment loss based on the obtained geometric alignment vector.

In this case, by reflecting the material property relationship characteristic information in the weight of at least one of the aforementioned losses during pre-training of the integrated prediction model, the integrated prediction model may be trained so that the relationship information between the material properties of multiple material properties is reflected.

Particularly, firstly, the computing system 1000 may compute regression loss.

In addition, secondly, the computing system 1000 may compute autoencoder loss based on the integrated prediction model that has obtained the geometric alignment vector. In addition, the computing system 1000 may learn a bidirectional transformation matrix (TM) that may be mapped to a common integrated latent space (M) for each task.

In addition, thirdly, the computing system 1000 may compute consistency loss based on the integrated prediction model that has obtained the geometric alignment vector.

In addition, fourthly, the computing system 1000 may compute mapping loss based on the integrated prediction model that has obtained the geometric alignment vector.

In addition, fifthly, the computing system 1000 may compute distance loss based on the integrated prediction model that has obtained the geometric alignment vector.

In addition, sixthly, the computing system 1000 may compute integrated loss based on the integrated prediction model that has obtained the geometric alignment vector.

The computing system 1000 may compute the integrated loss by weighted summing the regression loss, autoencoder loss, consistency loss, mapping loss, and distance loss described above according to [Equation 7] below.

$$L_{tot} = L_{reg} + \alpha L_{auto} + \beta L_{cons} + \gamma L_{map} + \delta L_{dis} \qquad \text{[Equation 7]}$$

The computing system 1000 may perform model optimization and parameter update based on the geometric alignment loss calculated as described above.

In addition, the computing system 1000 may adjust the weight for at least one loss of the integrated loss according to the determined material property relationship information, thereby more accurately reflecting the relationship information between material properties detected from the pre-studied specialized data.

In the above integrated loss, the loss in the relationship between material properties may be a mapping loss. Accordingly, the computing system 1000 may reflect the relationship information between material properties by determining or correcting the weight "γ" for the mapping loss according to the determined material property relationship information.

Particularly, when the first and second material properties are correlated and have a high association, the mapping loss weight may be increased to strengthen learning according to the mapping loss and reflect relationship information between the material properties. When there is no correlation between the first and second material properties or the association is low, the mapping loss weight may be lowered to weaken learning according to the mapping loss.

As such, the integrated prediction model that has simultaneously pre-trained prediction tasks for at least two material properties may naturally learn the correlations between material properties through transfer learning while learning a plurality of material properties, thereby making predictions for each material property more accurate.

In addition, when the experimental data for each material property includes data for different molecular structure types, the transfer learning may be used to train various molecular structure types, enabling accurate task performance for material properties of various molecular structures.

In other words, the integrated prediction model trained through the pre-training method of the above multi-tasking model may overcome this issue and provide accurate predictions when learning about common principles as well as local patterns by learning about the relationships between material properties. In addition, by learning multiple material properties simultaneously, it is possible to learn about a wider range of molecules by including all molecules that have data for each material property, thereby expanding the range of possible accurate predictions.

In addition, the computing system 1000 may provide various services through the integrated prediction model trained as such.

Particularly, the computing system 1000 inputs a specific molecular structural formula, inputs the molecular structural formula into the integrated prediction model, and outputs characteristic values for each of the plurality of material properties pre-trained by the integrated prediction model, thereby providing the characteristic values for the plurality of material properties. In this case, the characteristic values for each material property may be provided as a specific value with the highest probability and/or a range for a specific probability.

In addition, the computing system 1000 may provide a service that outputs at least one molecular structural formula that satisfies the characteristic values for the plurality of material properties by reverse engineering a pre-trained integrated prediction model and inputting characteristic values for each of the plurality of material properties.

[New Task Update Method for Predicting New Material Properties in Pre-Trained Integrated Prediction Model]

When a user requests the performance of a new task that has not been pre-trained, the integrated prediction model may quickly update the integrated prediction model based on the existing multi-tasking model pre-training method using only experimental data for the new task without performing full pre-training.

Herein, the new task may include a case where prediction is performed on a material property that has not been pre-trained, including cases where the material property is different and cases where the material property is the same but the experimental data is different. Herein, cases where the experimental data are different may be cited as examples, for example, the solubility in a first solvent and the solubility in a second solvent.

In detail, the computing system 1000 may obtain experimental data of the predicted target material property (S401).

Herein, the experimental data of the predicted target material property may be data including characteristic values of the predicted target material property for a plurality of materials.

Next, the computing system 1000 may trains an n-th prediction model that predicts the predicted target material property based on a pre-trained integrated prediction model (S403).

In detail, the n-th prediction model may include an n-th ECM, an n-th RGM, an nth TFM, and an n-th ITM corresponding to a specific task in a multi-tasking model.

The computing system 1000 may update the integrated prediction model by learning about the n-th prediction model through the experimental data of the predicted target material property while freezing modules for the task of predicting each pre-trained material property.

The computing system 1000 may perform learning that adds only learning for tasks added to a pre-trained model by having the n-th prediction model predict a characteristic value for the predicted target material property while simultaneously learning that the encoder vector is mapped to an integrated latent space by the transfer vector obtained through the TFM.

Through the integrated prediction model updated as such, the computing system 1000 may provide a service for predicting the plurality of material properties or a service for predicting material properties for the plurality of material properties.

Particularly, when the molecular structural formula of a material information to be predicted is input (S405), the computing system 1000 may input the material information into n-th prediction model and output predicted data regarding predicted target material property (S407) and provide predicted data regarding at least one material property regarding material information to be predicted (S409).

By updating new tasks based on the multi-tasking model pre-training method, when predictions for new tasks need to be made, the learning time may be significantly shortened by learning only for new tasks rather than retraining the model that predicts previously learned tasks from scratch. In addition, model performance may be improved compared to existing multi-task learning techniques through geometric alignment.

The embodiments of the present disclosure described above may be implemented in the form of program commands which may be executed through various types of computer constituting elements and recorded in a computer-readable recording medium. The computer-readable recording medium may include program commands, data files, and data structures separately or in combination thereof. The program commands recorded in the computer-readable recording medium may be those designed and configured specifically for the present disclosure or may be those commonly available for those skilled in the field of computer software. Examples of a computer-readable recoding medium may include magnetic media such as hard-disks, floppy disks, and magnetic tapes; optical media such as CD-ROMs and DVDs; and hardware devices specially designed to store and execute program commands such as ROM, RAM, and flash memory. Examples of program commands include not only machine codes such as those generated by a compiler but also high-level language codes which may be executed by a computer through an interpreter and the like. The hardware device may be replaced with by at least one software module configured to perform the operations of the present disclosure, and vice versa.

Specific executions described in the present disclosure are example, embodiments and the scope of the present disclosure is not limited even by any method. For brevity of the specification, descriptions of conventional electronic configurations, control systems, software, and other functional aspects of the systems may be omitted. Further, connection or connection members of lines among components exemplarily represent functions connections and/or physical or circuitry connections and may be represented as various functional connections, physical connections, or circuitry connections which are replaceable or added in an actual device. Further, unless otherwise specified, such as "essential" or "important," the connections may not be components particularly required for application of the present disclosure.

Further, in the detailed description of the present disclosure, which is described, while the present disclosure has been described with respect to the preferred embodiments, it will be understood by those skilled in the art or those skilled in the art having ordinary knowledge in the technical field that various changes and modifications of the present disclosure may be made without departing from the spirit and the technical scope of the invention described in the following claims. Accordingly, the technical scope of the present disclosure should not be limited to the contents described in the detailed description of the present disclosure but should be defined by the claims.

An embodiment of the present disclosure relates to a method and system for predicting a plurality of material properties, and is applicable to the artificial intelligence industry, and thus has industrial applicability.

An aspect of an embodiment of the present disclosure is directed to developing an integrated prediction model that predicts an integrated output that satisfies each of the plurality of domains using a pre-trained multi-tasking model as described above.

Another aspect of an embodiment of the present disclosure is directed to providing the integrated prediction model capable of predicting the plurality of material properties for a specific material by applying the integrated prediction model to predict a relationship between the plurality of material properties and materials and predicting a specific material that satisfies the plurality of material properties.

A method and system for predicting a plurality of material properties according to an embodiment of the present disclosure can provide a multi-tasking model that maintains high performance for multiple tasks even in a small data set by addressing the issue of insufficient data by transferring knowledge trained in a source task to a target task through transfer learning.

Accordingly, the method and system for predicting the plurality of material properties according to an embodiment of the present disclosure can expand the scope of application to fields where it was difficult to apply the machine learning model due to insufficient data or domain knowledge.

In addition, the method and system for predicting the plurality of material properties according to an embodiment of the present disclosure provide a specialized transfer learning technique that can be effectively applied to regression problems, thereby demonstrating high prediction performance even in complex regression problems such as molecular data sets.

In addition, the method and system for predicting the plurality of material properties according to an embodiment of the present disclosure can improve the efficiency of transfer learning by maintaining geometric consistency between tasks by optimizing knowledge transfer between source tasks and target tasks through a Riemannian geometric approach.

In addition, the method and system for predicting the plurality of material properties according to an embodiment of the present disclosure can further improve the generalization performance of the model by combining multiple loss functions to regularize various aspects of the model.

Accordingly, the method and system for predicting the plurality of material properties according to an embodiment of the present disclosure can provide prediction values for each domain in each of a plurality of domains through an integrated prediction model that simultaneously considers the plurality of domains.

In addition, the method and system for predicting the plurality of material properties according to an embodiment of the present disclosure can quickly update and provide an integrated prediction model capable of performing tasks in a new domain through rapid updates when data for a new domain that has not been pre-trained is added.

In addition, the method and system for predicting the plurality of material properties according to an embodiment of the present disclosure utilize an integrated prediction model to extract information for predicting a relationship between materials and the plurality of material properties, thereby predicting a material satisfying a plurality of specific material properties, or conversely, predicting the characteristics of each material property for a specific material.

Accordingly, the method and system for predicting the plurality of material properties according to an embodiment of the present disclosure provide a multi-tasking model that can be universally utilized for various materials (substances), thereby improving the quality of the related industry as a whole.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A method for a computing system including at least one memory and at least one processor configured to predict characteristics regarding a plurality of material properties, the method comprising:

obtaining experimental data including characteristics data on the plurality of material properties regarding materials;

pre-training an integrated prediction model for a plurality of tasks of predicting characteristics regarding the plurality of material properties from the obtained experimental data;

inputting, to the pre-trained integrated prediction model, material information to be predicted;

outputting, by the integrated prediction model, a characteristic value for each of the plurality of material properties in regard to the material information; and providing the output characteristic value for each of the plurality of material properties, wherein the pre-training of the integrated prediction model for the plurality of tasks comprises:

mapping a first feature vector corresponding to a first material property to an integrated latent space; and mapping a second feature vector corresponding to a second material property to the integrated latent space.

2. The method of claim 1, wherein the material information includes at least one piece of information of a molecular structural formula, a material name, or a chemical formula, each of the plurality of material properties includes at least one of a boiling point, a melting point, a refractive index, solubility, viscosity, surface tension, density, strength, or thermal conductivity, and the characteristic value for each material property includes a characteristic value or range predicted for the material property.

3. The method of claim 1, wherein the pre-training of the integrated prediction model for the plurality of tasks further includes:

training a source task module configured to perform a prediction on the first material property as a source task; and training a target task module configured to perform a prediction on the second material property as a target task, wherein the first feature vector is configured to predict the first material property and the second feature vector is configured to predict the second material property.

4. The method of claim 3, further comprising:

computing an integrated loss including a regression loss for training the source task module, an autoencoder loss for training the target task module, and a consistency loss and a mapping loss in a process of mapping the first feature vector to the integrated latent space; and training the integrated prediction model through the integrated loss.

5. The method of claim 4, further comprising:

generating a perturbation vector for an embedding vector for the material information;

computing a distance loss based on the perturbation vector; and adding the computed distance loss to the integrated loss.

6. The method of claim 1, wherein the pre-training of the integrated prediction model for the plurality of tasks includes:

obtaining a geometric alignment vector configured to support geometric alignment between data in one integrated latent space based on the experimental data;

computing a geometric alignment loss based on the obtained geometric alignment vector; and updating parameters of the integrated prediction model based on the computed geometric alignment loss.

7. The method of claim 1, wherein the pre-training of the integrated prediction model for the plurality of tasks includes pre-training the integrated prediction model based on material property relationship information between the material properties of the plurality of tasks.

8. The method of claim 7, wherein the pre-training of the integrated prediction model based on the material property relationship information includes:

obtaining material property relationship data indicating a relationship between the material properties; and storing the obtained material property relationship data in a material property relationship database.

9. The method of claim 8, wherein the obtaining of the material property relationship data indicating the relationship between the material properties includes collecting the material property relationship data including the material property relationship information by commanding a pre-trained language model configured to perform a keyword search for the material properties.

10. The method of claim 9, wherein the storage of the obtained material property relationship data in the material property relationship database includes:

extracting the material property relationship information from the material property relationship data through the language model; and classifying, characterizing, and storing information on the extracted material property relationship information.

11. The method of claim 10, wherein the material property relationship information includes information on the material properties associated with a specific material property, information configured to determine relationship characteristics such as trade-off, similarity, or correlation when associated, and information indicating the degree of association in the determined relationship characteristics.

12. The method of claim 11, further comprising:

providing a knowledge graph representing the material property relationship information.

13. The method of claim 11, wherein the pre-training of the integrated prediction model for the plurality of tasks includes performing pre-training on the integrated prediction model by reflecting the material property relationship information between the material properties of the plurality of tasks.

14. The method of claim 1, further comprising:

performing an update on the integrated prediction model for a new task other than the plurality of tasks.

15. The method of claim 14, wherein the performance of the update for the new task includes:

obtaining the experimental data of a predicted target material property of the new task; and training an n-th prediction model added to the pre-trained integrated prediction model through the experimental data of the predicted target material property.

16. The method of claim 15, wherein the training of the n-th prediction model through the experimental data of the predicted target material property includes updating the integrated prediction model by training a module included in the n-th prediction model through the experimental data while freezing the module related to a pre-trained task in the integrated prediction model.

17. The method of claim 16, wherein the provision of the output characteristic value for each of the plurality of material properties includes inputting the material information into the n-th prediction model to provide the characteristic value for each material property including the characteristic value predicted for a new material property.

18. A system for predicting a plurality of material properties, the system comprising:

at least one memory; and at least one processor including at least one instruction and configured to train an integrated prediction model by reading out at least one application stored in the memory, wherein the at least one processor is configured to:

obtain experimental data including characteristics data on the plurality of material properties regarding materials;

pre-train an integrated prediction model for a plurality of tasks of predicting characteristics regarding the plurality of material properties from the obtained experimental data;

input, to the pre-trained integrated prediction model, material information to be predicted;

output, by the integrated prediction model, a characteristic value for each of the plurality of material properties in regard to the material information; and provide the output characteristic value for each of the plurality of material properties, wherein the pre-training of the integrated prediction model for the plurality of tasks comprises:

mapping a first feature vector corresponding to a first material property to an integrated latent space; and mapping a second feature vector corresponding to a second material property to the integrated latent space.

19. The system of claim 18, wherein the material information includes at least one piece of information of a molecular structural formula, a material name, or a chemical formula, each of the plurality of material properties includes at least one of a boiling point, a melting point, a refractive index, solubility, viscosity, surface tension, density, strength, or thermal conductivity, and the characteristic value for each material property includes a characteristic value or range predicted for the material property.

20. The system of claim 18, wherein the pre-training of the integrated prediction model for the plurality of tasks further includes:

training a source task module configured to perform a prediction on the first material property as a source task; and training a target task module configured to perform a prediction on the second material property as a target task, wherein the first feature vector is configured to predict the first material property and the second feature vector is configured to predict the second material property.

* * * * *